(12) United States Patent
Woolf et al.

(10) Patent No.: US 10,479,992 B2
(45) Date of Patent: *Nov. 19, 2019

(54) RNA DUPLEXES WITH SINGLE STRANDED PHOSPHOROTHIOATE NUCLEOTIDE REGIONS FOR ADDITIONAL FUNCTIONALITY

(71) Applicant: Phio Pharmaceuticals Corp., Marlborough, MA (US)

(72) Inventors: Tod M. Woolf, Sudbury, MA (US); Joanne Kamens, Newton, MA (US); William Salomon, Worcester, MA (US); Anastasia Khvorova, Westborough, MA (US)

(73) Assignee: Phio Pharmaceuticals Corp., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/638,586

(22) Filed: Jun. 30, 2017

(65) Prior Publication Data

US 2018/0155718 A1 Jun. 7, 2018

Related U.S. Application Data

(63) Continuation of application No. 13/147,882, filed as application No. PCT/US2010/000348 on Feb. 4, 2010, now Pat. No. 9,745,574.

(60) Provisional application No. 61/149,968, filed on Feb. 4, 2009, provisional application No. 61/150,582, filed on Feb. 6, 2009, provisional application No. 61/163,306, filed on Mar. 25, 2009.

(51) Int. Cl.
*C12N 15/11* (2006.01)
*C12N 15/113* (2010.01)
*A61K 31/713* (2006.01)

(52) U.S. Cl.
CPC ........ *C12N 15/111* (2013.01); *C12N 2310/11* (2013.01); *C12N 2310/14* (2013.01); *C12N 2310/321* (2013.01); *C12N 2310/322* (2013.01); *C12N 2310/3515* (2013.01); *C12N 2310/3519* (2013.01); *C12N 2310/533* (2013.01); *C12N 2320/51* (2013.01)

(58) Field of Classification Search
CPC .............. C12N 15/111; C12N 2320/30; A61K 2300/00; C12Q 1/6886
USPC .............. 435/6.1, 91.1, 91.31, 455; 514/44; 536/23.1, 24.5
See application file for complete search history.

(56) References Cited

U.S. PATENT DOCUMENTS

| 3,687,808 A | 8/1972 | Merigan et al. |
|---|---|---|
| 4,201,860 A | 5/1980 | Naito et al. |
| 4,235,871 A | 11/1980 | Papahadjopoulos et al. |
| 4,384,975 A | 5/1983 | Fong |
| 4,389,330 A | 6/1983 | Tice et al. |
| 4,415,732 A | 11/1983 | Caruthers et al. |
| 4,426,330 A | 1/1984 | Sears |
| 4,469,863 A | 9/1984 | Ts'o et al. |
| 4,476,301 A | 10/1984 | Imbach et al. |
| 4,501,728 A | 2/1985 | Geho et al. |
| 4,652,441 A | 3/1987 | Okada et al. |
| 4,737,323 A | 4/1988 | Martin et al. |
| 4,837,028 A | 6/1989 | Allen |
| 4,897,355 A | 1/1990 | Eppstein et al. |
| 4,904,582 A | 2/1990 | Tullis |
| 4,958,013 A | 9/1990 | Letsinger |
| 5,013,556 A | 5/1991 | Woodle et al. |
| 5,023,243 A | 6/1991 | Tullis |
| 5,034,506 A | 7/1991 | Summerton et al. |
| 5,051,257 A | 9/1991 | Pietronigro |
| 5,053,228 A | 10/1991 | Mori et al. |
| 5,108,921 A | 4/1992 | Low et al. |
| 5,112,963 A | 5/1992 | Pieles et al. |
| 5,149,782 A | 9/1992 | Chang et al. |
| 5,151,510 A | 9/1992 | Stec et al. |
| 5,162,115 A | 11/1992 | Pietronigro |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,213,804 A | 5/1993 | Martin et al. |
| 5,214,134 A | 5/1993 | Weis et al. |
| 5,216,141 A | 6/1993 | Benner |
| 5,227,170 A | 7/1993 | Sullivan |

(Continued)

FOREIGN PATENT DOCUMENTS

AU 2004206255 B2 8/2004
CN 1 568 373 A 1/2005
(Continued)

OTHER PUBLICATIONS

Blalock et al., Connective tissue growth factor expression and action in human corneal fibroblast cultures and rat corneas after photorefractive keratectomy. Invest Ophthalmol Vis Sci. May 2003;44(5):1879-87.

(Continued)

*Primary Examiner* — Jane J Zara

(74) *Attorney, Agent, or Firm* — Wolf, Greenfield & Sacks, P.C.

(57) ABSTRACT

The present invention relates to RNAi constructs and their use in gene silencing. RNAi constructs associated with the invention contain a double stranded region connected to a single stranded region of phosphorothioate modified nucleotides.

20 Claims, 11 Drawing Sheets

Specification includes a Sequence Listing.

(56) References Cited

U.S. PATENT DOCUMENTS

| | | |
|---|---|---|
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,284,656 A | 2/1994 | Platz et al. |
| 5,286,717 A | 2/1994 | Cohen et al. |
| 5,321,131 A | 6/1994 | Agrawal et al. |
| 5,354,844 A | 10/1994 | Beug et al. |
| 5,356,633 A | 10/1994 | Woodle et al. |
| 5,391,723 A | 2/1995 | Priest |
| 5,399,676 A | 3/1995 | Froehler |
| 5,405,938 A | 4/1995 | Summerton et al. |
| 5,405,939 A | 4/1995 | Suhadolnik |
| 5,416,016 A | 5/1995 | Low et al. |
| 5,416,203 A | 5/1995 | Letsinger |
| 5,417,978 A | 5/1995 | Tari et al. |
| 5,432,272 A | 7/1995 | Benner |
| 5,434,257 A | 7/1995 | Matteucci et al. |
| 5,451,569 A | 9/1995 | Wong et al. |
| 5,453,496 A | 9/1995 | Caruthers et al. |
| 5,455,233 A | 10/1995 | Spielvogel et al. |
| 5,459,127 A | 10/1995 | Felgner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,486,603 A | 1/1996 | Buhr |
| 5,489,677 A | 2/1996 | Sanghvi et al. |
| 5,495,009 A | 2/1996 | Matteucci et al. |
| 5,512,667 A | 4/1996 | Reed et al. |
| 5,514,786 A | 5/1996 | Cook et al. |
| 5,519,126 A | 5/1996 | Hecht |
| 5,525,465 A | 6/1996 | Haralambidis |
| 5,527,528 A | 6/1996 | Allen et al. |
| 5,527,899 A | 6/1996 | Froehler |
| 5,532,130 A | 7/1996 | Alul |
| 5,534,259 A | 7/1996 | Zalipsky et al. |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,556,948 A | 9/1996 | Tagawa et al. |
| 5,561,225 A | 10/1996 | Maddry et al. |
| 5,563,253 A | 10/1996 | Agrawal et al. |
| 5,565,555 A | 10/1996 | Froehler et al. |
| 5,571,799 A | 11/1996 | Tkachuk et al. |
| 5,574,142 A | 11/1996 | Meyer, Jr. et al. |
| 5,578,718 A | 11/1996 | Cook et al. |
| 5,580,731 A | 12/1996 | Chang et al. |
| 5,580,972 A | 12/1996 | Tu et al. |
| 5,583,020 A | 12/1996 | Sullivan |
| 5,587,361 A | 12/1996 | Cook et al. |
| 5,587,469 A | 12/1996 | Cook et al. |
| 5,591,721 A | 1/1997 | Agrawal et al. |
| 5,591,722 A | 1/1997 | Montgomery et al. |
| 5,591,843 A | 1/1997 | Eaton |
| 5,594,121 A | 1/1997 | Froehler et al. |
| 5,596,086 A | 1/1997 | Matteucci et al. |
| 5,596,091 A | 1/1997 | Switzer |
| 5,599,797 A | 2/1997 | Cook et al. |
| 5,602,240 A | 2/1997 | De Mesmaeker et al. |
| 5,607,923 A | 3/1997 | Cook et al. |
| 5,608,046 A | 3/1997 | Cook et al. |
| 5,610,289 A | 3/1997 | Cook et al. |
| 5,614,617 A | 3/1997 | Cook et al. |
| 5,614,621 A | 3/1997 | Ravikumar et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,643,889 A | 7/1997 | Suhadolnik et al. |
| 5,646,126 A | 7/1997 | Cheng et al. |
| 5,646,265 A | 7/1997 | McGee |
| 5,646,269 A | 7/1997 | Matteucci et al. |
| 5,658,731 A | 8/1997 | Sproat et al. |
| 5,661,134 A | 8/1997 | Cook et al. |
| 5,663,312 A | 9/1997 | Chaturvedula |
| 5,670,633 A | 9/1997 | Cook et al. |
| 5,672,697 A | 9/1997 | Buhr et al. |
| 5,674,683 A | 10/1997 | Kool |
| 5,677,437 A | 10/1997 | Teng et al. |
| 5,677,439 A | 10/1997 | Weis et al. |
| 5,681,940 A | 10/1997 | Wang et al. |
| 5,681,941 A | 10/1997 | Cook et al. |
| 5,684,143 A | 11/1997 | Gryaznov et al. |
| 5,697,248 A | 12/1997 | Brown |
| 5,700,920 A | 12/1997 | Altmann et al. |
| 5,721,218 A | 2/1998 | Froehler |
| RE546,678 | 4/1998 | Buhr et al. |
| 5,736,392 A | 4/1998 | Hawley-Nelson et al. |
| 5,750,666 A | 5/1998 | Caruthers et al. |
| 5,767,099 A | 6/1998 | Harris et al. |
| 5,770,713 A | 6/1998 | Imbach et al. |
| 5,777,153 A | 7/1998 | Lin et al. |
| 5,780,053 A | 7/1998 | Ashley et al. |
| 5,780,607 A | 7/1998 | Goodnow, Jr. et al. |
| 5,789,416 A | 8/1998 | Lum et al. |
| 5,792,608 A | 8/1998 | Swaminathan et al. |
| 5,792,847 A | 8/1998 | Buhr et al. |
| 5,808,023 A | 9/1998 | Sanghvi et al. |
| 5,814,014 A | 9/1998 | Elsberry et al. |
| 5,817,781 A | 10/1998 | Swaminathan et al. |
| 5,830,430 A | 11/1998 | Unger et al. |
| 5,830,653 A | 11/1998 | Froehler et al. |
| 5,849,902 A | 12/1998 | Arrow et al. |
| 5,851,548 A | 12/1998 | Dattagupta et al. |
| 5,855,910 A | 1/1999 | Ashley et al. |
| 5,856,455 A | 1/1999 | Cook |
| 5,874,553 A | 2/1999 | Peyman et al. |
| 5,914,396 A | 6/1999 | Cook et al. |
| 5,945,521 A | 8/1999 | Just et al. |
| 5,948,767 A | 9/1999 | Scheule et al. |
| 5,969,116 A | 10/1999 | Martin |
| 5,976,567 A | 11/1999 | Wheeler et al. |
| 5,981,501 A | 11/1999 | Wheeler et al. |
| 5,986,083 A | 11/1999 | Dwyer et al. |
| 6,001,841 A | 12/1999 | Cook et al. |
| 6,005,094 A | 12/1999 | Simon et al. |
| 6,005,096 A | 12/1999 | Matteucci et al. |
| 6,015,886 A | 1/2000 | Dale et al. |
| 6,020,475 A | 2/2000 | Capaldi et al. |
| 6,020,483 A | 2/2000 | Beckvermit et al. |
| 6,028,183 A | 2/2000 | Lin et al. |
| 6,033,910 A | 3/2000 | Monia et al. |
| 6,043,352 A | 3/2000 | Manoharan et al. |
| 6,051,699 A | 4/2000 | Ravikumar |
| 6,093,180 A | 7/2000 | Elsberry |
| 6,096,875 A | 8/2000 | Khan et al. |
| 6,107,094 A | 8/2000 | Crooke |
| 6,111,085 A | 8/2000 | Cook et al. |
| 6,121,437 A | 9/2000 | Guzaev |
| 6,127,346 A | 10/2000 | Peyman et al. |
| 6,133,229 A | 10/2000 | Gibson et al. |
| 6,153,737 A | 11/2000 | Manoharan et al. |
| 6,172,208 B1 | 1/2001 | Cook |
| 6,207,819 B1 | 3/2001 | Manoharan et al. |
| 6,210,892 B1 | 4/2001 | Bennett et al. |
| 6,242,594 B1 | 6/2001 | Kelly |
| 6,248,878 B1 | 6/2001 | Matulic-Adamic et al. |
| 6,262,241 B1 | 7/2001 | Cook et al. |
| 6,271,358 B1 | 8/2001 | Manoharan et al. |
| 6,299,895 B1 | 10/2001 | Hammang et al. |
| 6,300,319 B1 | 10/2001 | Manoharan |
| 6,326,358 B1 | 12/2001 | Manoharan |
| 6,331,313 B1 | 12/2001 | Wong et al. |
| 6,331,617 B1 | 12/2001 | Weeks et al. |
| 6,335,434 B1 | 1/2002 | Guzaev et al. |
| 6,335,437 B1 | 1/2002 | Manoharan |
| 6,344,436 B1 | 2/2002 | Smith et al. |
| 6,346,416 B1 | 2/2002 | Dean et al. |
| 6,355,787 B1 | 3/2002 | Beckvermit et al. |

(56) References Cited

U.S. PATENT DOCUMENTS

| | | |
|---|---|---|
| 6,358,931 B1 | 3/2002 | Cook et al. |
| 6,378,526 B1 | 4/2002 | Bowman et al. |
| 6,395,474 B1 | 5/2002 | Buchardt et al. |
| 6,395,492 B1 | 5/2002 | Manoharan et al. |
| 6,397,849 B1 | 6/2002 | Bowman et al. |
| 6,399,754 B1 | 6/2002 | Cook |
| 6,410,702 B1 | 6/2002 | Swaminathan et al. |
| 6,420,549 B1 | 7/2002 | Cook et al. |
| 6,432,963 B1 | 8/2002 | Hisamichi et al. |
| 6,436,427 B1 | 8/2002 | Hammang et al. |
| 6,440,943 B1 | 8/2002 | Cook |
| 6,444,806 B1 | 9/2002 | Veerapanani et al. |
| 6,455,586 B1 | 9/2002 | Kaplan et al. |
| 6,465,628 B1 | 10/2002 | Ravikumar et al. |
| 6,476,205 B1 | 11/2002 | Buhr et al. |
| 6,506,559 B1 | 1/2003 | Fire et al. |
| 6,525,031 B2 | 2/2003 | Manoharan |
| 6,528,631 B1 | 3/2003 | Cook et al. |
| 6,531,584 B1 | 3/2003 | Cook et al. |
| 6,559,279 B1 | 5/2003 | Manoharan et al. |
| 6,656,730 B1 | 12/2003 | Manoharan |
| 6,673,611 B2 | 1/2004 | Thompson et al. |
| 6,683,167 B2 | 1/2004 | Meteley et al. |
| 6,815,432 B2 | 11/2004 | Wheeler et al. |
| 6,849,726 B2 | 2/2005 | Usman et al. |
| 6,858,225 B2 | 2/2005 | Semple et al. |
| 6,887,906 B1 | 5/2005 | Teng et al. |
| 7,041,824 B2 | 5/2006 | Bordon-Pallier et al. |
| 7,056,704 B2 | 6/2006 | Tuschl et al. |
| 7,078,196 B2 | 7/2006 | Tuschl et al. |
| 7,132,530 B2 | 11/2006 | Bennett et al. |
| 7,148,342 B2 | 12/2006 | Tolentino et al. |
| 7,205,297 B2 | 4/2007 | Beauchamp et al. |
| 7,432,250 B2 | 10/2008 | Crooke |
| 7,521,431 B2 | 4/2009 | Reich et al. |
| 7,538,095 B2 | 5/2009 | Fire et al. |
| 7,560,438 B2 | 7/2009 | Fire et al. |
| 7,595,387 B2 | 9/2009 | Leake et al. |
| 7,605,251 B2 | 10/2009 | Tan et al. |
| 7,622,455 B2 | 11/2009 | Bennett et al. |
| 7,622,633 B2 | 11/2009 | Fire et al. |
| 7,629,321 B2 | 12/2009 | Crooke |
| 7,695,902 B2 | 4/2010 | Crooke |
| 7,745,608 B2 | 6/2010 | Manoharan et al. |
| 7,750,144 B2 | 7/2010 | Zamore et al. |
| 7,786,290 B2 | 8/2010 | Woppmann et al. |
| 7,829,693 B2 | 11/2010 | Kreutzer et al. |
| 7,838,507 B2 | 11/2010 | Shepard et al. |
| 7,902,163 B2 | 3/2011 | Bennett et al. |
| 8,110,674 B2 | 2/2012 | Manoharan et al. |
| 8,168,600 B2 | 5/2012 | Dokka et al. |
| 8,202,845 B2 | 6/2012 | Drumm et al. |
| 8,263,569 B2 | 9/2012 | Baulcombe et al. |
| 8,268,794 B2 | 9/2012 | Nakajima et al. |
| 8,383,600 B2 | 2/2013 | Czech et al. |
| 8,470,792 B2 | 6/2013 | Frost et al. |
| 8,664,189 B2 | 3/2014 | Khvorova et al. |
| 8,796,443 B2 | 8/2014 | Khvorova et al. |
| 8,815,818 B2 | 8/2014 | Samarsky et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,222,092 B2 | 12/2015 | Giese et al. |
| 9,303,259 B2 | 4/2016 | Khvorova et al. |
| 9,340,786 B2 | 5/2016 | Khvorova et al. |
| 9,493,774 B2 | 11/2016 | Kamens |
| 9,745,574 B2 * | 8/2017 | Woolf .................. C12N 15/111 |
| 9,938,530 B2 | 4/2018 | Khvorova et al. |
| 9,963,702 B2 | 5/2018 | Khvorova et al. |
| 10,041,073 B2 | 8/2018 | Khvorova et al. |
| 10,131,904 B2 | 11/2018 | Pavco et al. |
| 10,138,485 B2 | 11/2018 | Khvorova et al. |
| 10,167,471 B2 | 1/2019 | Kamens et al. |
| 10,184,124 B2 | 1/2019 | Libertine et al. |
| 10,240,149 B2 | 3/2019 | Khvorova et al. |
| 10,300,027 B2 | 5/2019 | Levis et al. |
| 2002/0049173 A1 | 4/2002 | Bennett et al. |
| 2002/0081736 A1 | 6/2002 | Conroy et al. |
| 2002/0132788 A1 | 9/2002 | Lewis et al. |
| 2002/0147332 A1 | 10/2002 | Kaneko et al. |
| 2002/0160393 A1 | 10/2002 | Symonds et al. |
| 2002/0162126 A1 | 10/2002 | Beach et al. |
| 2003/0004325 A1 | 1/2003 | Cook et al. |
| 2003/0027780 A1 | 2/2003 | Hardee et al. |
| 2003/0077829 A1 | 4/2003 | MacLachlan |
| 2003/0108923 A1 | 6/2003 | Tuschl et al. |
| 2003/0139585 A1 | 7/2003 | Uhlmann et al. |
| 2003/0148979 A1 | 8/2003 | Sosnowski et al. |
| 2003/0153524 A1 | 8/2003 | Hinton et al. |
| 2003/0157030 A1 | 8/2003 | Davis et al. |
| 2003/0158403 A1 | 8/2003 | Manoharan et al. |
| 2003/0166282 A1 | 9/2003 | Brown et al. |
| 2004/0009938 A1 | 1/2004 | Manoharan et al. |
| 2004/0014957 A1 | 1/2004 | Eldrup et al. |
| 2004/0018999 A1 | 1/2004 | Beach et al. |
| 2004/0054155 A1 | 3/2004 | Woolf et al. |
| 2004/0063654 A1 | 4/2004 | Davis et al. |
| 2004/0072785 A1 | 4/2004 | Wolff et al. |
| 2004/0102618 A1 | 5/2004 | Crooke et al. |
| 2004/0137471 A1 | 7/2004 | Vickers et al. |
| 2004/0162235 A1 | 8/2004 | Trubetskoy et al. |
| 2004/0167090 A1 | 8/2004 | Monahan et al. |
| 2004/0171033 A1 | 9/2004 | Baker et al. |
| 2004/0180351 A1 | 9/2004 | Giese et al. |
| 2004/0192629 A1 | 9/2004 | Xu et al. |
| 2004/0204377 A1 | 10/2004 | Rana |
| 2004/0219520 A1 | 11/2004 | Mirkin et al. |
| 2004/0229266 A1 | 11/2004 | Tuschl et al. |
| 2004/0241845 A1 | 12/2004 | Desgroseillers et al. |
| 2004/0248839 A1 | 12/2004 | Kowalik |
| 2004/0259247 A1 | 12/2004 | Tuschl et al. |
| 2005/0008617 A1 | 1/2005 | Chen et al. |
| 2005/0020521 A1 | 1/2005 | Rana |
| 2005/0026286 A1 | 2/2005 | Chi et al. |
| 2005/0032733 A1 | 2/2005 | McSwiggen et al. |
| 2005/0037496 A1 | 2/2005 | Rozema et al. |
| 2005/0042227 A1 | 2/2005 | Zankel et al. |
| 2005/0064595 A1 | 3/2005 | MacLachlan et al. |
| 2005/0080246 A1 | 4/2005 | Allerson et al. |
| 2005/0107325 A1 | 5/2005 | Manoharan et al. |
| 2005/0142535 A1 | 6/2005 | Damha et al. |
| 2005/0181382 A1 | 8/2005 | Zamore et al. |
| 2005/0239731 A1 | 10/2005 | McSwiggen et al. |
| 2005/0245474 A1 | 11/2005 | Baker et al. |
| 2005/0246794 A1 | 11/2005 | Khvorova et al. |
| 2005/0255487 A1 | 11/2005 | Khvorova et al. |
| 2005/0265957 A1 | 12/2005 | Monahan et al. |
| 2005/0281781 A1 | 12/2005 | Ostroff |
| 2006/0008910 A1 | 1/2006 | MacLachlan et al. |
| 2006/0009409 A1 | 1/2006 | Woolf |
| 2006/0069050 A1 | 3/2006 | Rana |
| 2006/0127891 A1 | 6/2006 | McSwiggen et al. |
| 2006/0142228 A1 | 6/2006 | Ford et al. |
| 2006/0160133 A1 | 7/2006 | Czech et al. |
| 2006/0178324 A1 | 8/2006 | Hadwiger et al. |
| 2006/0178327 A1 | 8/2006 | Yeung |
| 2006/0211766 A1 | 9/2006 | Kaplan et al. |
| 2006/0229268 A1 | 10/2006 | Benjamin et al. |
| 2006/0234970 A1 | 10/2006 | Jimenez |
| 2006/0240093 A1 | 10/2006 | MacLachlan et al. |
| 2007/0032441 A1 | 2/2007 | McSwiggen et al. |
| 2007/0087989 A1 | 4/2007 | Huang et al. |
| 2007/0166734 A1 | 7/2007 | Bhat et al. |
| 2007/0173473 A1 | 7/2007 | McSwiggen et al. |
| 2007/0173476 A1 | 7/2007 | Leake et al. |
| 2007/0231392 A1 | 10/2007 | Wagner et al. |
| 2007/0269889 A1 | 11/2007 | Leake et al. |
| 2008/0038296 A1 | 2/2008 | Brahmbhatt et al. |
| 2008/0071068 A1 | 3/2008 | Oba et al. |
| 2008/0085869 A1 | 4/2008 | Yamada et al. |
| 2008/0107694 A1 | 5/2008 | Trogden et al. |
| 2008/0108583 A1 | 5/2008 | Feinstein et al. |
| 2008/0112916 A1 | 5/2008 | Wagner et al. |

(56) References Cited

U.S. PATENT DOCUMENTS

| | | |
|---|---|---|
| 2008/0125386 A1 | 5/2008 | Rana et al. |
| 2008/0152654 A1 | 6/2008 | Reich |
| 2008/0152661 A1 | 6/2008 | Rozema et al. |
| 2008/0242851 A1 | 10/2008 | Khvorova et al. |
| 2008/0311040 A1 | 12/2008 | Berry et al. |
| 2009/0023216 A1 | 1/2009 | Woolf |
| 2009/0131360 A1 | 5/2009 | Woolf et al. |
| 2009/0171075 A1 | 7/2009 | Li |
| 2009/0182136 A1 | 7/2009 | Wengel et al. |
| 2009/0186802 A1 | 7/2009 | Alluis et al. |
| 2009/0208564 A1 | 8/2009 | Li et al. |
| 2009/0239814 A1 | 9/2009 | Manoharan et al. |
| 2009/0247608 A1 | 10/2009 | Manoharan et al. |
| 2009/0306005 A1 | 12/2009 | Bhanot et al. |
| 2010/0010082 A1 | 1/2010 | Chong et al. |
| 2010/0040656 A1 | 2/2010 | Franklin et al. |
| 2010/0047188 A1 | 2/2010 | Kandimalla et al. |
| 2010/0069620 A1 | 3/2010 | Zon |
| 2010/0081705 A1 | 4/2010 | Bennett et al. |
| 2010/0136695 A1 | 6/2010 | Woolf |
| 2010/0331812 A1 | 12/2010 | Friden et al. |
| 2011/0021605 A1 | 1/2011 | Schulte et al. |
| 2011/0039914 A1 | 2/2011 | Pavco et al. |
| 2011/0237522 A1 | 9/2011 | Khvorova et al. |
| 2011/0237648 A1 | 9/2011 | Khvorova et al. |
| 2011/0251258 A1 | 10/2011 | Samarsky et al. |
| 2011/0263680 A1 | 10/2011 | Khvorova et al. |
| 2011/0268761 A1 | 11/2011 | Levis et al. |
| 2011/0269813 A1 | 11/2011 | Unger |
| 2011/0288147 A1 | 11/2011 | Brown et al. |
| 2011/0294869 A1 | 12/2011 | Petersen |
| 2012/0016005 A1 | 1/2012 | Samarsky et al. |
| 2012/0040459 A1 | 2/2012 | Khvorova et al. |
| 2012/0059046 A1 | 3/2012 | Woolf et al. |
| 2013/0131141 A1 | 5/2013 | Khvorova et al. |
| 2013/0131142 A1 | 5/2013 | Libertine et al. |
| 2013/0197055 A1 | 8/2013 | Kamens et al. |
| 2014/0072613 A1 | 3/2014 | Lander et al. |
| 2014/0113950 A1 | 4/2014 | Khvorova et al. |
| 2014/0315974 A1 | 10/2014 | Khvorova et al. |
| 2014/0364482 A1 | 12/2014 | Khvorova et al. |
| 2015/0057362 A1 | 2/2015 | Levis et al. |
| 2016/0115482 A1 | 4/2016 | Libertine et al. |
| 2016/0115484 A1 | 4/2016 | Woolf et al. |
| 2016/0130578 A1 | 5/2016 | Khvorova et al. |
| 2016/0244765 A1 | 8/2016 | Khvorova et al. |
| 2016/0304873 A1 | 10/2016 | Wolfson et al. |
| 2016/0304875 A1 | 10/2016 | Cauwenbergh et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2017/0009239 A1 | 1/2017 | Khvorova et al. |
| 2017/0051288 A1 | 2/2017 | Byrne et al. |
| 2017/0051290 A1 | 2/2017 | Byrne et al. |
| 2017/0067056 A1 | 3/2017 | Khvorova et al. |
| 2017/0137823 A1 | 5/2017 | Kamens et al. |
| 2018/0030451 A1 | 2/2018 | Cauwenbergh |
| 2018/0195066 A1 | 7/2018 | Byrne et al. |
| 2018/0195072 A1 | 7/2018 | Cardia et al. |
| 2018/0263925 A1 | 9/2018 | Cauwenbergh et al. |
| 2018/0327748 A1 | 11/2018 | Khvorova et al. |
| 2018/0371464 A1 | 12/2018 | Khvorova et al. |
| 2019/0029974 A1 | 1/2019 | Cauwenbergh et al. |
| 2019/0048341 A1 | 2/2019 | Cardia et al. |
| 2019/0161757 A1 | 5/2019 | Khvorova et al. |

FOREIGN PATENT DOCUMENTS

| | | |
|---|---|---|
| CN | 101160138 A | 4/2008 |
| EP | 0 552 766 A2 | 7/1993 |
| EP | 1 214 945 A2 | 6/2002 |
| EP | 1 144 623 B9 | 3/2003 |
| EP | 1 352 061 B1 | 10/2003 |
| EP | 0 928 290 B9 | 3/2005 |
| EP | 1 407 044 B1 | 9/2007 |
| EP | 1 605 978 B1 | 9/2010 |
| JP | H09-505057 A | 5/1997 |
| JP | 4 095 895 B2 | 9/2004 |
| JP | 2005-519881 A | 7/2005 |
| JP | 2006-516288 A | 6/2006 |
| JP | 2007-525169 A | 9/2007 |
| JP | 2007-531520 A | 11/2007 |
| JP | 2009-519033 | 5/2009 |
| JP | 2010-501188 A | 1/2010 |
| JP | 2013-523650 A | 6/2013 |
| WO | 89/02439 A1 | 3/1989 |
| WO | 90/14074 A1 | 11/1990 |
| WO | 91/16024 A1 | 10/1991 |
| WO | 91/17424 A1 | 11/1991 |
| WO | 92/03464 A1 | 3/1992 |
| WO | 94/23028 A2 | 10/1994 |
| WO | 95/06731 A2 | 3/1995 |
| WO | 95/11910 A1 | 5/1995 |
| WO | 95/13827 A1 | 5/1995 |
| WO | 95/23162 A1 | 8/1995 |
| WO | 96/40964 A2 | 12/1996 |
| WO | 99/13915 A1 | 3/1999 |
| WO | 99/60012 A1 | 11/1999 |
| WO | 03/012052 A2 | 2/2003 |
| WO | 03/049773 A1 | 6/2003 |
| WO | 2003/064626 A2 | 8/2003 |
| WO | 2003/087367 A2 | 10/2003 |
| WO | 2003/087368 A2 | 10/2003 |
| WO | 2004/042027 A2 | 5/2004 |
| WO | 2004/064760 A2 | 8/2004 |
| WO | 2004/065600 A2 | 8/2004 |
| WO | 2004/065601 A2 | 8/2004 |
| WO | 2004/090105 A2 | 10/2004 |
| WO | 2005/019430 A2 | 3/2005 |
| WO | 2005/019453 A2 | 3/2005 |
| WO | 2005/024033 A2 | 3/2005 |
| WO | 2005/078096 A2 | 8/2005 |
| WO | 2005/079533 A2 | 9/2005 |
| WO | 2005/097992 A2 | 10/2005 |
| WO | 2006/007372 A2 | 1/2006 |
| WO | 2006/019430 A2 | 2/2006 |
| WO | 2006/039656 A2 | 4/2006 |
| WO | 2006/065601 A2 | 6/2006 |
| WO | 2006/069037 A1 | 6/2006 |
| WO | 2006/128141 A2 | 11/2006 |
| WO | 2007/021142 A1 | 2/2007 |
| WO | 2007/030167 A1 | 3/2007 |
| WO | 2007/044362 A2 | 4/2007 |
| WO | 2007/050643 A2 | 5/2007 |
| WO | 2007/069068 A2 | 6/2007 |
| WO | 2007/089607 A2 | 8/2007 |
| WO | 2008/021157 A1 | 2/2008 |
| WO | 2008/024983 A2 | 2/2008 |
| WO | 2008/036825 A2 | 3/2008 |
| WO | 2008/109353 A1 | 9/2008 |
| WO | 2008/125908 A2 | 10/2008 |
| WO | 2009/020344 A2 | 2/2009 |
| WO | 2009/029688 A3 | 3/2009 |
| WO | 2009/029690 A1 | 3/2009 |
| WO | 2009/044392 A2 | 4/2009 |
| WO | 2009/045457 A2 | 4/2009 |
| WO | 2009/078685 A2 | 6/2009 |
| WO | 2009/126933 A2 | 10/2009 |
| WO | 2010/006237 A2 | 1/2010 |
| WO | 2010/011346 A2 | 1/2010 |
| WO | 2010/027830 A2 | 3/2010 |
| WO | 2010/033246 A1 | 3/2010 |
| WO | 2010/033247 A2 | 3/2010 |
| WO | 2010/042281 A2 | 4/2010 |
| WO | 2011/109698 A1 | 9/2011 |
| WO | 2011/119871 A1 | 9/2011 |
| WO | 2014/191493 A1 | 12/2014 |
| WO | 2015/031392 A1 | 3/2015 |

OTHER PUBLICATIONS

Byrne et al., Novel hydrophobically modified asymmetric RNAi compounds (sd-rxRNA) demonstrate robust efficacy in the eye. J

(56) References Cited

OTHER PUBLICATIONS

Ocul Pharmacol Ther. Dec. 2013;29(10):855-64. doi: 10.1089/jop.2013.0148. Epub Nov. 1, 2013.

Chung et al., Immunohistochemical study on the aggregation of ubiquitin in the central nervous system of the transgenic mice expressing a human Cu/Zn SOD mutation. Neurol Res. Jun. 2003;25(4):395-400.

Crooke et al., Silencing of P2Y2 receptor delays Ap4A-corneal re-epithelialization process. Mol Vis. Jun. 11, 2009;15:1169-78.

Cruthirds et al., Mitochondrial targets of oxidative stress during renal ischemia/reperfusion. Arch Biochem Biophys. Apr. 1, 2003;412(1):27-33.

Cudkowicz et al., Epidemiology of mutations in superoxide dismutase in amyotrophic lateral sclerosis. Ann Neurol. Feb. 1997;41(2):210-21.

De Belleroche et al, Familial amyotrophic lateral sclerosis/motor neurone disease (FALS): a review of current developments. J Med Genet. Nov. 1995;32(11):841-7.

Flanagan et al., Overexpression of manganese superoxide dismutase attenuates neuronal death in human cells expressing mutant (G37R) Cu/Zn-superoxide dismutase. J Neurochem. Apr. 2002;81(1):170-7.

GenBank Submission; NIH/NCBI, Accession No. NM_000454.4. Homo sapiens superoxide dismutase 1 (SOD1), mRNA. May 12, 2019. 6 pages.

Hagigit et al., Ocular antisense oligonucleotide delivery by cationic nanoemulsion for improved treatment of ocular neovascularization: an in-vivo study in rats and mice. J Control Release. Jun. 10, 2012;160(2):225-31. doi: 10.1016/j.jconrel.2011.11.022. Epub Nov. 27, 2011.

Hao et al., Electrically assisted delivery of macromolecules into the corneal epithelium. Exp Eye Res. Dec. 2009;89(6):934-41. doi: 10.1016/j.exer.2009.08.001. Epub Aug. 12, 2009.

Hao et al., Gene delivery to cornea. Brain Res Bull. Feb. 15, 2010;81(2-3):256-61. doi: 10.1016/j.brainresbull.2009.06.011. Epub Jun. 26, 2009. Review.

Hartong et al., Retinitis pigmentosa. Lancet. Nov. 18, 2006;368(9549):1795-809.

Hinton et al., Novel growth factors involved in the pathogenesis of proliferative vitreoretinopathy. Eye (Lond). Jul. 2002;16(4):422-8.

Hosseini et al., Efficacy of a phosphorodiamidate morpholino oligomer antisense compound in the inhibition of corneal transplant rejection in a rat cornea transplant model. J Ocul Pharmacol Ther. Apr. 2012;28(2):194-201. doi: 10.1089/jop.2011.0135. Epub Dec. 7, 2011.

Jaarsma et al., Human Cu/Zn superoxide dismutase (SOD1) overexpression in mice causes mitochondrial vacuolization, axonal degeneration, and premature motoneuron death and accelerates motoneuron disease in mice expressing a familial amyotrophic lateral sclerosis mutant SOD1. Neurobiol Dis. Dec. 2000;7(6 Pt B):623-43.

Jones et al., Cu/Zn superoxide dismutase (SOD1) mutations and sporadic amyotrophic lateral sclerosis. Lancet. Oct. 23, 1993;342(8878):1050-1.

Kiningham et al., All-trans-retinoic acid induces manganese superoxide dimutase in human neuroblastoma through NF-kappaB. Free Radic Biol Med. Apr. 15, 2008;44(8):1610-6, doi: 10.1016/j.freeradbiomed.2008.01.015. Epub Jan. 30, 2008. Author manuscript.

Lebovitz et al., Neurodegeneration, myocardial injury, and perinatal death in mitochondrial superoxide dismutase-deficient mice. Proc Natl Acad Sci U S A. Sep. 3, 1996;93(18):9782-7.

Li et al., A new approach of delivering siRNA to the cornea and its application for inhibiting herpes simplex keratitis. Curr Mol Med. 2014;14(9):1215-25. Database Embase Abstract only. Accession No. EMB-2015893176.

Maehara et al., a NF-kappaB p65 subunit is indispensable for activating manganese superoxide: dismutase gene transcription mediated by tumor necrosis factor-alpha. J Cell Biochem. Apr. 2000;77(3):474-86.

Palomo et al., Exploring new pathways of neurodegeneration in ALS: the role of mitochondria quality control. Brain Res. May 14, 2015;1607:36-46. doi: 10.1016/j.brainres.2014.09.065. Epub Oct. 6, 2014. Author manuscript.

Parone et al., Enhancing mitochondrial calcium buffering capacity reduces aggregation of misfolded SOD1 and motor neuron cell death without extending survival in mouse models of inherited amyotrophic lateral sclerosis. J Neurosci. Mar. 13, 2013;33(11):4657-71. doi: 10.1523/Jneurosci.1119-12.2013.

Ramamurthi et al., Pathogenesis, clinical features and management of recurrent corneal erosions. Eye (Lond). Jun. 2006;20(6):635-44. Epub Jul. 15, 2005.

Rose et al., Functional polarity is introduced by Dicer processing of short substrate RNAs. Nucleic Acids Res. Jul. 26, 2005;33(13):4140-56. Print 2005.

Sherwood et al., A sequential, multiple-treatment, targeted approach to reduce wound healing and failure of glaucoma filtration surgery in a rabbit model (an American Ophthalmological Society thesis). Trans Am Ophthalmol Soc. 2006;104:478-92.

Sriram et al., Reduction of corneal scarring in rabbits by targeting the TGFB1 pathway with a triple siRNA combination. Adv Biosci Biotechnol. Jan. 1, 2013;4(10):47-55.

Sriram et al., Triple combination of siRNAs targeting TGFβ1, TGFβR2, and CTGF enhances reduction of collagen I and smooth muscle actin in corneal fibroblasts. Invest Ophthalmol Vis Sci. Dec. 17, 2013;54(13):8214-23. doi: 10.1167/iovs.13-12758.

Strong et al., The pathobiology of amyotrophic lateral sclerosis: a proteinopathy? J Neuropathol Exp Neurol. Aug. 2005;64(8):649-64.

Swarup et al., ALS pathogenesis: recent insights from genetics and mouse models. Prog Neuropsychopharmacol Biol Psychiatry. Mar. 30, 2011;35(2):363-9. doi: 10.1016/j.pnpbp.2010.08.006. Epub Aug. 20, 2010.

Toyono et al., Angiopoietin-like protein 2 is a potent hemangiogenic and lymphangiogenic factor in corneal inflammation. Invest Ophthalmol Vis Sci. Jun. 26, 2013;54(6):4278-85. doi: 10.1167/iovs.12-11497.

Visner et al., Regulation of manganese superoxide dismutase by lipopolysaccharide, interleukin-1, and tumor necrosis factor. Role in the acute inflammatory response. J Biol Chem. Feb. 15, 1990;265(5):2856-64.

Wasmuth et al., Topical antisense-oligonucleotides targeting IFN-gamma mRNA improve incidence and severity of herpetic stromal keratitis by cytokine specific and sequence unspecific effects. Graefes Arch Clin Exp Ophthalmol. Mar. 2008;246(3):443-51. Epub Nov. 21, 2007.

Wright et al., Screening for inhibitors of the SOD1 gene promoter: pyrimethamine does not reduce SOD1 levels in cell and animal models. Neurosci Lett. Oct. 4, 2010;482(3):188-92. doi: 10.1016/j.neulet.2010.07.020. Epub Jul. 16, 2010. Author manuscript.

[No Author Listed] RedChip Small-Cap Investor Conference. RXI Pharmaceuticals (Nasdaq RXII). Jun. 16, 2009 Presentation. 22 pages.

[No Author Listed] Rxi Pharmaceutical Corporation. Ex 99.1. OTC: RXII. Mar. 2013. 38 pages.

[No Author Listed], Rxi Pharmaceuticals Presents Self-Delivering RNAi Data at Scar Club Meeting in France. Drugs.com. Mar. 26, 2010. http://www.drugs.com/clinical_trials/rxi-pharmaceuticals-presents-self-delivering-rnai-data-scar-club-meeting-france-9093.html [last accessed Aug. 19, 2014].

Akinc et al., Development of lipidoid-siRNA formulations for systemic delivery to the liver. Mol Ther. May 2009;17(5):872-9. doi: 10.1038/mt.2009.36. Epub Mar. 3, 2009.

Alahari et al., Inhibition of expression of the multidrug resistance-associated P-glycoprotein of by phosphorothioate and 5' cholesterol-conjugated phosphorothioate antisense oligonucleotides. Mol Pharmacol. Oct. 1996;50(4):808-19.

Aleckovic et al., J RNAi Gene Silencing. May 27, 2008;4(1):266-8.

Augustyns et al., Incorporation of hexose nucleoside analogues into oligonucleotides: synthesis, base-pairing properties and enzymatic stability. Nucleic Acids Res. Sep. 25, 1992;20(18):4711-6.

Baigude et al., Design and creation of new nanomaterials for therapeutic RNAi. ACS Chem Biol. Apr. 24, 2007;2(4):237-41.

Bartzatt, Cotransfection of nucleic acid segments by Sendai virus envelopes. Biotechnol Appl Biochem. Feb. 1989;11(1):133-5.

(56) References Cited

OTHER PUBLICATIONS

Bergan et al., Electroporation enhances c-myc antisense oligodeoxynucleotide efficacy. Nucleic Acids Res. Jul. 25, 1993;21(15):3567-73.

Bertrand et al., Comparison of antisense oligonucleotides and siRNAs in cell culture and in vivo. Biochem Biophys Res Commun. Aug. 30, 2002;296(4):1000-4.

Bjergarde et al., Solid phase synthesis of oligodeoxyribonucleoside phosphorodithioates from thiophosphoramidites. Nucleic Acids Res. Nov. 11, 1991;19(21):5843-50.

Bongartz et al., Improved biological activity of antisense oligonucleotides conjugated to a fusogenic peptide. Nucleic Acids Res. Nov. 11, 1994;22(22):4681-8.

Boutorin et al., Synthesis of alkylating oligonucleotide derivatives containing cholesterol or phenazinium residues at their 3'-terminus and their interaction with DNA within mammalian cells. FEBS Lett. Aug. 28, 1989;254(1-2):129-32.

Braasch et al., RNA interference in mammalian cells by chemically-modified RNA. Biochemistry. Jul. 8, 2003;42(26):7967-75.

Brown et al., RNAi off-targeting: Light at the end of the tunnel. J RNAi Gene Silencing. Jul. 28, 2006;2(2):175-7.

Bunnell et al., Targeted delivery of antisense oligonucleotides by molecular conjugates. Somat Cell Mol Genet. Nov. 1992;18(6):559-69.

Cardia et al., Novel self-delivering RNAi compounds with enhanced cellular updatake and distribution properties. Keystone RNAi Silencing Conference. Jan. 14-19, 2010. Poster. 1 Page.

Chen et al., Functionalization of single-walled carbon nanotubes enables efficient intracellular delivery of siRNA targeting MDM2 to inhibit breast cancer cells growth. Biomed Pharmacother. Jul. 2012;66(5):334-8. doi: 10.1016/j.biopha.2011.12.005. Epub Feb. 17, 2012.

Chen et al., Nanoparticles modified with tumor-targeting scFv deliver siRNA and miRNA for cancer therapy. Mol Ther. Sep. 2010;18(9):1650-6. doi: 10.1038/mt.2010.136. Epub Jul. 6, 2010.

Chiang et al., Antisense oligonucleotides inhibit intercellular adhesion molecule 1 expression by two distinct mechanisms. J Biol Chem. Sep. 25, 1991;266(27):18162-71.

Chiu et al., siRNA function in RNAi: a chemical modification analysis. RNA. Sep. 2003;9(9):1034-48.

Chiu et al., Visualizing a correlation between siRNA localization, cellular uptake, and RNAi in living cells. Chem Biol. Aug. 2004;11(8):1165-75.

Choung et al., Chemical modification of siRNAs to improve serum stability without loss of efficacy. Biochem Biophys Res Commun. Apr. 14, 2006;342(3):919-27.

Chu et al., Potent RNAi by short RNA triggers. RNA. 2008;14:1714-9.

Cload et al., Polyether tethered oligonucleotide probes. Journal of the American Chemical Society. 1991;113 (16): 6324-6326.

Collins et al., a small interfering RNA screen for modulators of tumor cell motility identifies MAP4K4 as a promigratory kinase. Proc Natl Acad Sci U S A. Mar. 7, 2006; 103(10): 3775-3780.

Constantinides et al., Formulation and intestinal absorption enhancement evaluation of water-in-oil microemulsions incorporating medium-chain glycerides. Pharm Res. Oct. 1994;11(10):1385-90.

Crombez et al., A non-covalent peptide-based strategy for siRNA delivery. Biochem Soc Trans. Feb. 2007;35(Pt 1):44-6. Review.

Czauderna et al., Structural variations and stabilising modifications of synthetic siRNAs in mammalian cells. Nucleic Acids Res. Jun. 1, 2003;31(11):2705-16.

De Smidt et al., Association of antisense oligonucleotides with lipoproteins prolongs the plasma half-life and modifies the tissue distribution. Nucleic Acids Res. Sep. 11, 1991;19(17):4695-700.

Debart et al., Chemical modifications to improve the cellular uptake of oligonucleotides. Curr Top Med Chem. 2007;7(7):727-37.

Durand et al., Circular dichroism studies of an oligodeoxyribonucleotide containing a hairpin loop made of a hexaethylene glycol chain: conformation and stability. Nucleic Acids Res. Nov. 11, 1990;18(21):6353-9.

Dykxhoorn et al., the silent treatment: siRNAs as small molecule drugs. Gene Ther. Mar. 2006;13(6):541-52. Review.

Eichelbaum et al., Influence of pharmacogenetics on drug disposition and response. Clin Exp Pharmacol Physiol. Oct.-Nov. 1996;23(10-11):983-5. Review.

Elbashir et al., Duplexes of 21-nucleotide RNAs mediate RNA interference in cultured mammalian cells. Nature. May 24, 2001;411(6836):494-8.

Elbashir et al., Functional anatomy of siRNAs for mediating efficient RNAi in *Drosophila melanogaster* embryo lysate. Embo J. Dec. 3, 2001;20(23):6877-88.

Fedorov et al., Off-target effects by siRNA can induce toxic phenotype. RNA. Jul. 2006;12(7):1188-96. Epub May 8, 2006.

Ferentz et al., Disulfide-crosslinked oligonucleotides. Journal of the American Chemical Society. 1991;113 (10): 4000-4002.

Fisher et al., Intracellular disposition and metabolism of fluorescently-labeled unmodified and modified oligonucleotides microinjected into mammalian cells. Nucleic Acids Res. Aug. 11, 1993;21(16):3857-65.

Flanagan et al., A cytosine analog that confers enhanced potency to antisense oligonucleotides. Proc Natl Acad Sci U S A. Mar. 30, 1999;96(7):3513-8.

Florence, The oral absorption of micro- and nanoparticulates: neither exceptional nor unusual. Pharm Res. Mar. 1997;14(3):259-66.

Frank-Kamenetsky et al., Therapeutic RNAi targeting PCSK9 acutely lowers plasma cholesterol in rodents and LDL cholesterol in non-human primates. Proc Natl Acad Sci U S A. Aug. 19, 2008;105(33):11915-20. doi: 10.1073/pnas.0805434105. Epub Aug. 11, 2008.

Fritz et al., Gene transfer into mammalian cells using histone-condensed plasmid DNA. Hum Gene Ther. Aug. 1, 1996;7(12):1395-404.

Gaudana et al., Ocular drug delivery. AAPS J. Sep. 2010;12(3):348-60. doi: 10.1208/s12248-010-9183-3. Epub May 1, 2010.

Genbank Submission; NCBI, Accession No. NM_004834; Bouzakri et al., Oct. 24, 2008. 8 Pages.

Grosse et al., in vivo gene delivery in the mouse lung with lactosylated polyethylenimine, questioning the relevance of in vitro experiments. J Control Release. Dec. 8, 2008;132(2):105-12. Epub Sep. 4, 2008.

Ho et al., Preparation of microemulsions using polyglycerol fatty acid esters as surfactant for the delivery of protein drugs. J Pharm Sci. Feb. 1996;85(2):138-43.

Holmes et al., Syntheses and oligonucleotide incorporation of nucleoside analogues containing pendant imidazolyl or amino functionalities—the search for sequence-specific artificial ribonucleases. Eur J Org Chem. Apr. 13, 2005;5171-83. DOI; 10.1002/ejoc.20050413.

Huang et al., Lipitoids—novel cationic lipids for cellular delivery of plasmid DNA in vitro. Chem Biol. Jun. 1998;5(6):345-54.

Jablonski et al., Preparation of oligodeoxynucleotide-alkaline phosphatase conjugates and their use as hybridization probes. Nucleic Acids Res. Aug. 11, 1986;14(15):6115-28.

Jackson et al., Position-specific chemical modification of siRNAs reduces "off-target" transcript silencing. RNA. Jul. 2006;12(7):1197-1205. Epub May 8, 2006.

Kamata et al., Amphiphilic peptides enhance the efficiency of liposome-mediated DNA transfection. Nucleic Acids Res. Feb. 11, 1994;22(3):536-7.

Kamens et al., Novel, chemically modified RNAi compounds with improved potency, stability and specificity. Keystone RNAi Silencing: Mechanism, Biology and Application Conference. Jan. 14-19, 2010. Poster. 1 Page.

Kawasaki et al., Uniformly modified 2'-deoxy-2'-fluoro phosphorothioate oligonucleotides as nuclease-resistant antisense compounds with high affinity and specificity for RNA targets. J Med Chem. Apr. 2, 1993;36(7):831-41.

Kim et al., Systemic and specific delivery of small interfering RNAs to the liver mediated by apolipoprotein A-I. Mol Ther. Jun. 2007;15(6):1145-52. Epub Apr. 17, 2007.

(56) References Cited

OTHER PUBLICATIONS

Kraynack et al., Small interfering RNAs containing full 2'-O-methylribonucleotide-modified sense strands display Argonaute2/eIF2C2-dependent activity. RNA. Jan. 2006;12(1):163-76. Epub Nov. 21, 2005.
Kubo et al., Modified 27-nt dsRNAs with dramatically enhanced stability in serum and longterm RNAi activity. Oligonucleotides. 2007 Winter;17(4):445-64.
Layzer et al., in vivo activity of nuclease-resistant siRNAs. RNA. May 2004;10(5):766-71.
Lee et al., Contributions of 3'-overhang to the dissociation of small interfering RNAs from the PAZ domain: molecular dynamics simulation study. J Mol Graph Model. Mar. 2007;25(6):784-93. Epub Jul. 11, 2006.
Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.
Leuschner et al., Cleavage of the siRNA passenger strand during RISC assembly in human cells. EMBO Reports 2006;7(3):314-20.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Li et al., Surface-modified LPD nanoparticles for tumor targeting. Ann N Y Acad Sci. Oct. 2006;1082:1-8.
Ma et al., Design and synthesis of RNA miniduplexes via a synthetic linker approach. Biochemistry. Feb. 23, 1993;32(7):1751-8.
Ma et al., Design and synthesis of RNA miniduplexes via a synthetic linker approach. 2. Generation of covalently closed, double-stranded cyclic HIV-1 TAR RNA analogs with high Tat-binding affinity. Nucleic Acids Res. Jun. 11, 1993;21(11):2585-9.
Manoharan et al., Chemical modifications to improve uptake and bioavailability of antisense oligonucleotides. Ann N Y Acad Sci. Oct. 28, 1992;660:306-9.
Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.
Martins et al., Sterol side chain length and structure affect the clearance of chylomicron-like lipid emulsions in rats and mice. J Lipid Res. Feb. 1998;39(2):302-12.
Mathews et al., Incorporating chemical modification constraints into a dynamic programming algorithm for prediction of RNA secondary structure. Proc Natl Acad Sci U S A. May 11, 2004;101(19):7287-92. Epub May 3, 2004.
McCurdy, et al., Deoxyoligonucleotides with inverted polarity: synthesis and use in triple-helix formation. Nucleosides & Nucleotides. 1991;10(1-3):287-290. Epub Aug. 29, 2007.
Medarova et al., In vivo imaging of siRNA delivery and silencing in tumors. Nat Med. Mar. 2007;13(3):372-7. Epub Feb. 25, 2007.
Mescalchin et al., Cellular uptake and intracellular release are major obstacles to the therapeutic application of siRNA: novel options by phosphorothioate-stimulated delivery. Expert Opin Biol Ther. Oct. 2007;7(10):1531-8. Review.
Mistry et al., Recombinant HMG1 protein produced in Pichia pastoris: a nonviral gene delivery agent. Biotechniques. Apr. 1997;22(4):718-29.
Murphy et al., A combinatorial approach to the discovery of efficient cationic peptoid reagents for gene delivery. Proc Natl Acad Sci U S A. Feb. 17, 1998;95(4):1517-22.
Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.
Ono et al., DNA triplex formation of oligonucleotide analogues consisting of linker groups and octamer segments that have opposite sugar-phosphate backbone polarities. Biochemistry. Oct. 15, 1991;30(41):9914-2.
Opalinska et al., Nucleic-acid therapeutics: basic principles and recent applications. Nat Rev Drug Discov. Jul. 2002;1(7):503-14.
Ortigão et al., Antisense effect of oligodeoxynucleotides with inverted terminal internucleotidic linkages: a minimal modification protecting against nucleolytic degradation. Antisense Res Dev. 1992 Summer;2(2):129-46.
Overhoff et al., Phosphorothioate-stimulated uptake of short interfering RNA by human cells. EMBO Rep. Dec. 2005;6(12):1176-81.
Parrish et al., Functional anatomy of a dsRNA trigger: differential requirement for the two trigger strands in RNA interference. Mol Cell. Nov. 2000;6(5):1077-87.
Patel et al., Ocular drug delivery systems: An overview. World J Pharmacol. 2013;2(2):47-64. Author manuscript.
Pavco et al., Robust Intradermal efficacy with novel chemically modified self-delivering RNAi compounds. Keystone RNAi Silencing Conference: Mechanism, Biology and Application Conference. Jan. 14-19, 2010. Poster. 1 Page.
Rajeev et al., 2'-modified-2-thiothymidine oligonucleotides. Org Lett. Aug. 21, 2003;5(17):3005-8.
Richardson et al., Tethered oligonucleotide probes. A strategy for the recognition of structured RNA. Journal of the American Chemical Society. 1991;113 (13):5109-5111.
Rozema et al., Dynamic PolyConjugates for targeted in vivo delivery of siRNA to hepatocytes. Proc Natl Acad Sci U S A. Aug. 7, 2007; 104(32): 12982-12987.
Rozners et al., Expanding functionality of RNA: synthesis and properties of RNA containing imidazole modified tandem G-U wobble base pairs. Chem Commun (Camb). Dec. 14, 2005;(46):5778-80.
Rump et al., Preparation of conjugates of oligodeoxynucleotides and lipid structures and their interaction with low-density lipoprotein. Bioconjug Chem. May-Jun. 1998;9(3):341-9.
Salomon et al., Modified dsRNAs that are not processed by Dicer maintain potency and are incorporated into the RISC. Nucleic Acids Res. Jun. 2010;38(11):3771-9. doi: 10.1093/nar/gkq055. Epub Feb. 18, 2010.
Sato et al., Tumor targeting and imaging of intraperitoneal tumors by use of antisense oligo-DNA complexed with dendrimers and/or avidin in mice. Clin Cancer Res. Nov. 2001;7(11):3606-12.
Seela et al., Oligodeoxyribonucleotides containing 1,3-propanediol as nucleoside substitute. Nucleic Acids Res. Apr. 10, 1987;15(7):3113-29.
Shen, Advances in the development of siRNA-based therapeutics for cancer. IDrugs. Aug. 2008;11(8):572-8. Review.
Shi, Mammalian RNAi for the masses. Trends Genet. Jan. 2003;19(1):9-12.
Shoeman et al., Fluorescence microscopic comparison of the binding of phosphodiester and phosphorothioate (antisense) oligodeoxyribonucleotides to subcellular structures, including intermediate filaments, the endoplasmic reticulum, and the nuclear interior. Antisense Nucleic Acid Drug Dev. Aug. 1997;7(4):291-308.
Smith et al., Pulmonary deposition and clearance of aerosolized alpha-1-proteinase inhibitor administered to dogs and to sheep. J Clin Invest. Oct. 1989;84(4):1145-54.
Smith et al., The murine haemopexin receptor. Evidence that the haemopexin-binding site resides on a 20 kDa subunit and that receptor recycling is regulated by protein kinase C. Biochem J. Jun. 1, 1991;276 ( Pt 2):417-25.
Snead et al., RNA interference trigger variants: getting the most out of RNA for RNA interference-based therapeutics. Nucleic Acid Ther. Jun. 2012;22(3):139-46. doi: 10.1089/nat.2012.0361. Review.
Soto et al., Characterization of multilayered nanoparticles encapsulated in yeast cell wall particles for DNA delivery. Bioconjug Chem. Apr. 2008;19(4):840-8. doi: 10.1021/bc700329p. Epub Apr. 1, 2008.
Soto et al., Oral Macrophage Mediated Gene Delivery System. 2007 NSTI Nanotechnology Conference and Trade Show, May 20-24, 2007, Santa Clara, CA. NSTI Nanotech 2007 Proceedings; 2:378-81.
Soutschek et al., Therapeutic silencing of an endogenous gene by systemic administration of modified siRNAs. Nature. Nov. 11, 2004;432(7014):173-8.

(56) References Cited

OTHER PUBLICATIONS

Stein et al., A specificity comparison of four antisense types: morpholino, 2'-O-methyl RNA, DNA, and phosphorothioate DNA. Antisense Nucleic Acid Drug Dev. Jun. 1997;7(3):151-7.
Sui et al., a DNA vector-based RNAi technology to suppress gene expression in mammalian cells. Proc Natl Acad Sci U S A. Apr. 16, 2002;99(8):5515-20.
Summerton et al., Morpholino and phosphorothioate antisense oligomers compared in cell-free and in-cell systems. Antisense Nucleic Acid Drug Dev. Apr. 1997;7(2):63-70.
Summerton et al., Morpholino antisense oligomers: design, preparation, and properties. Antisense Nucleic Acid Drug Dev. Jun. 1997;7(3):187-95. Review.
Summerton, Morpholino antisense oligomers: the case for an RNase H-independent structural type. Biochim Biophys Acta. Dec. 1999;1489(1):141-58. Review.
Sun et al., Asymmetric RNA duplexes mediate RNA interference in mammalian cells. Nat Biotechnol. Dec. 2008;26(12):1379-82. doi: 10.1038/nbt.1512. Epub Nov. 23, 2008. 4 Pages.
Tan et al., Quantum-dot based nanoparticles for targeted silencing of HER2/neu gene via RNA interference. Biomaterials. Mar. 2007;28(8):1565-71. Epub Dec. 11, 2006.
Tang et al., an RNA interference-based screen identifies MAP4K4/NIK as a negative regulator of PPARgamma, adipogenesis, and insulin-responsive hexose transport. Proc Natl Acad Sci U S A. Feb. 14, 2006;103(7):2087-92. Epub Feb. 3, 2006.
Uhlmann et al., Antisense oligonucleotides: a new therapeutic principle. Chem Rev. 1990;90(4):543-84.
Vaught et al., Expanding the chemistry of DNA for in vitro selection. J Am Chem Soc. Mar. 31, 2010;132(12):4141-51. doi: 10.1021/ja908035g.
Vlassov et al., Transport of oligonucleotides across natural and model membranes. Biochim Biophys Acta. Jun. 29, 1994;1197(2):95-108.
Wolfrum et al., Mechanisms and optimization of in vivo delivery of lipophilic siRNAs. Nat Biotechnol. Oct. 2007;25(10):1149-57. Epub Sep. 16, 2007.
Wu et al., Durable protection from Herpes Simplex Virus-2 transmission following intravaginal application of siRNAs targeting both a viral and host gene. Cell Host Microbe. Jan. 22, 2009;5(1):84-94. doi:10.1016/j.chom.2008.12.003.
Wu et al., Receptor-mediated in vitro gene transformation by a soluble DNA carrier system. J Biol Chem. Apr. 5, 1987;262(10):4429-32. Erratum in: J Biol Chem Jan. 5, 1988;263(1):588.
Xue et al., Mesodermal patterning defect in mice lacking the Ste20 NCK interacting kinase (NIK). Development. May 2001;128(9):1559-72.
Yamada et al., Synthesis and properties of oligonucleotides having a chemically stable 2-(trimethylsilyl)benzoyl group. Nucleic Acids Symp Ser (Oxf). 2008;(52):301-2. doi: 10.1093/nass/nrn152.
Yu et al., RNA interference by expression of short-interfering RNAs and hairpin RNAs in mammalian cells. Proc Natl Acad Sci U S A. Apr. 30, 2002;99(9):6047-52. Epub Apr. 23, 2002.
Zhou et al., Controlled release of PEI/DNA complexes from mannose-bearing chitosan microspheres as a potent delivery system to enhance immune response to HBV DNA vaccine. J Control Release. Aug. 28, 2007;121(3):200-7. Epub May 25, 2007.
Zimmermann et al., RNAi-mediated gene silencing in non-human primates. Nature. May 4, 2006;441(7089):111-4. Epub Mar. 26, 2006.
Zuckermann et al., Design, construction and application of a fully automated equimolar peptide mixture synthesizer. Int J Pept Protein Res. Dec. 1992;40(6):497-506.
Zuckermann et al., Efficient method for the preparation of peptoids [oligo(N-substituted glycines)] by submonomer solid-phase synthesis. Journal of the American Chemical Society. 1992;114 (26):10646-10647.
U.S. Appl. No. 16/153,424, filed Oct. 5, 2018, Pavco et al.
U.S. Appl. No. 16/191,396, filed Nov. 14, 2018, Kamens et al.
U.S. Appl. No. 16/159,590, filed Oct. 12, 2018, Khvorova et al.
U.S. Appl. No. 16/270,524, filed Feb. 7, 2019, Khvorova et al.
U.S. Appl. No. 16/206,064, filed Nov. 30, 2018, Libertine et al.
U.S. Appl. No. 16/377,617, filed Apr. 8, 2019, Levis et al.

* cited by examiner

Figure 2
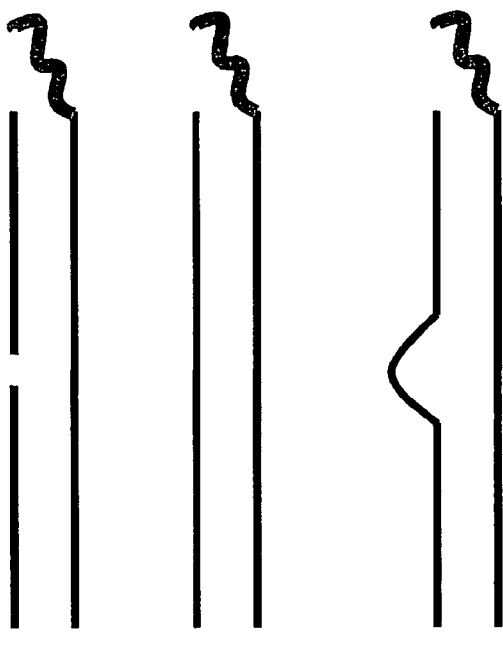
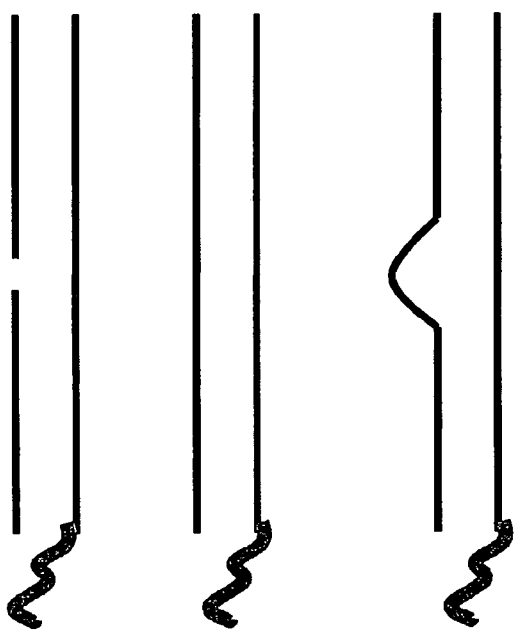

Figure 10

Summary of Results with PPIB Active Constructs using 25-bp Blunt ended dsRNA with PS DNA Tail

| Duplex ID | Description of Construct | Result |
|---|---|---|
| A | 12-bp Tail on 3' Sense with 12/10 modified Sense strand | Dramatic loss of activity, possibly active at high concentrations >5nM |
| B | 20-bp Tail on 3' Sense with 12/10 modified Sense strand | Not active |
| H | 12-bp Tail on 5' Sense with 12/10 modified Sense strand | Dramatic loss of activity, possibly active at high concentrations >5nM |
| I | 12-bp Tail on 5' Sense with unmodified Sense strand | Activity equal to rxRNA (picomolar EC50) |

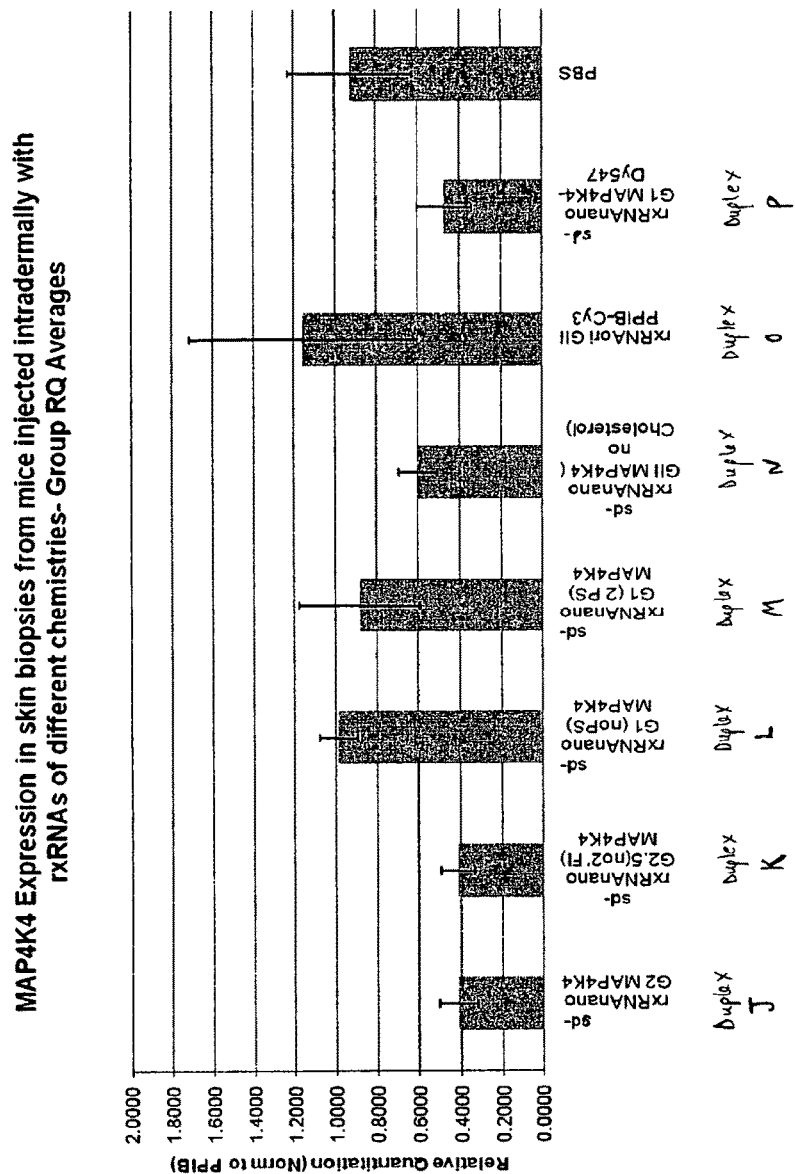

RNA DUPLEXES WITH SINGLE STRANDED PHOSPHOROTHIOATE NUCLEOTIDE REGIONS FOR ADDITIONAL FUNCTIONALITY

RELATED APPLICATIONS

This application is a continuation of, and claims the benefit under 35 U.S.C. § 120 to, U.S. application Ser. No. 13/147,882, entitled "RNA Duplexes with Single Stranded Phosphorothioate Nucleotide Regions for Additional Functionality" filed on Nov. 18, 2011, which is a national stage filing under 35 U.S.C. § 371 of international application PCT/US2010/000348, filed Feb. 4, 2010, which was published under PCT Article 21(2) in English, and claims the benefit under 35 U.S.C. § 119(e) of U.S. provisional application Ser. No. 61/149,968, entitled "PS Tail Constructs for RNA Delivery and Functionality," filed on Feb. 4, 2009, U.S. 61/150,582, entitled "PS Tail Constructs for RNA Delivery and Functionality," filed on Feb. 6, 2009, and U.S. 61/163,306, entitled "RNA Duplexes with Single Stranded Phosphorothioate Nucleotide Regions for Additional Functionality," filed on Mar. 25, 2009, the disclosures of each of which are incorporated by reference herein in their entirety.

FIELD OF INVENTION

The invention pertains to the field of RNA interference. The invention in some aspects includes nucleic acid molecules containing a double stranded region connected to a single stranded region of phosphorothioate modified nucleotides.

BACKGROUND OF INVENTION

Complementary oligonucleotide sequences are promising therapeutic agents and useful research tools in elucidating gene functions. However, prior art oligonucleotide molecules suffer from several problems that may impede their clinical development, and frequently make it difficult to achieve intended efficient inhibition of gene expression (including protein synthesis) using such compositions.

For example, classic siRNAs have limitations and drawbacks that may result in those agents being only moderately useful as human therapeutics. Specifically, classic siRNA is double-stranded. For each molecule, two strands need to be synthesized and paired up. Classic siRNA is made from naturally occurring ribonucleotides and is vulnerable to nucleases and spontaneous hydrolysis. The strands of classic siRNA are paired to each other except for an overhang of one strand at each end, and are about 19 to 23 nucleotides long. This configuration limits the variety and activity of the compound. For example, longer oligonucleotides can have higher binding activity to target RNA, which often correlates with higher activity. The overhangs of classic siRNA cause instability (because single strands are more nuclease resistant than double strands in most cases) and degradation, and may be the cause of the molecules "sticking" to each other or other nucleotides.

In addition, it is widely believed that double-stranded RNAs longer than 21-mer are cleaved by Dicer or Dicer-like RNAse III in mammalian cells, resulting in classic siRNA products. One strand of the Dicer-cleavage products is then loaded onto the RISC complex, and guides the loaded RISC complex to effect RNA interference (RNAi). However, since Dicer is not sequence specific, the Dicer-cleavage products of unmodified long dsRNA is a heterogeneous mixture of 21-mers, each may have different biological activity and/or pharmacological property. In addition, each 21-mer may have a distinct off-target effect (e.g., inhibiting the function of an unintended target due to, for example, spurious sequence homology between the Dicer cleavage product and target mRNAs). In other words, the active drug (e.g., the 21-mers) may be multiple species with relatively unpredictable target specificities, biological activities and/or pharmacological properties. Also, Dicer product is shorter than the parent, which leads to a lower affinity guide strand.

Other problems include the susceptibility of the siRNAs to non-specific nuclease degradation when applied to biological systems. Therefore, it would be of great benefit to improve upon the prior art oligonucleotides by designing improved oligonucleotides that either are free of or have reduced degree of the above-mentioned problems.

SUMMARY OF INVENTION

Described herein are RNAi constructs containing single stranded regions of phosphorothioate modified nucleotides, and the uses of such constructs in gene silencing. Aspects of the invention relate to isolated double stranded nucleic acid molecules including a guide strand and a passenger strand, wherein the passenger strand is connected through a cleavable linker to a single stranded region of at least eight phosphorothioate modified nucleotides.

In an aspect, the invention is an isolated double stranded nucleic acid molecule having a guide strand and a passenger strand, wherein at least one of the guide strand and passenger strand is connected through a cleavable linker to a single stranded region of at least six phosphorothioate modified nucleotides.

In another aspect the invention is an isolated double stranded nucleic acid molecule having a guide strand and a passenger strand, wherein at least one of the guide strand and passenger strand is connected through a cleavable linker to a single stranded region of at least three phosphorothioate modified nucleotides. In aspects, the double stranded nucleic acid molecule includes at least one of the following properties. The passenger strand may be 8-18 nucleotides in length. The nucleic acid may have at least one 2' O methyl or 2' fluoro modification. The cleavable linkage may be other than a nucleotidic linkage. The nucleic acid may include a lipophilic group. The guide strand may be 16-18 nucleotides or 26-28 nucleotides in length.

In some embodiments the single stranded region is connected to the guide strand.

In some embodiments, the cleavable linker includes one or more unmodified nucleotides. In other embodiments, the cleavable linker is a phosphodiester bond. In certain embodiments, the cleavable linker is S—S. In some embodiments the cleavable linker is DNA or RNA.

The single stranded region of at least eight phosphorothioate modified nucleotides can be at either the 3' or 5' end of the passenger strand. In some embodiments, the single stranded region of at least eight phosphorothioate modified nucleotides is DNA, while in other embodiments it is RNA.

In some embodiments the double stranded region of the nucleic acid molecule is a perfect duplex. In other embodiments the double stranded region contains at least one bulge region. In some embodiments the passenger strand comprises a nick within the double stranded region of the molecule. The double stranded region may contain at least one nucleotide that is phosphorothioate modified.

The nucleic acid molecules associated with the invention may be chemically modified. In certain embodiments the chemical modification is 2'Omethyl and/or 2'Fluoro. In some embodiments more than one chemical modification is present in the same molecule. In some embodiments chemical modification increases stability, increases evasion of immune regulation, and/or prevents off-target gene silencing. Chemical modification can be present on the passenger strand and/or the guide strand.

In some embodiments the single stranded region of at least eight phosphorothioate modified nucleotides is cleaved from the double stranded region of the nucleic acid molecule in a cell. In some embodiments the single stranded region of at least eight phosphorothioate modified nucleotides has complementarity to a mammalian gene. In certain embodiments the single stranded region of at least eight phosphorothioate modified nucleotides functions as an antisense molecule. The double stranded region may be at least 19 nucleotides long. In some embodiments the single stranded region is at least 12 nucleotides long.

Aspects of the invention relate to bifunctional nucleic acid molecule including a double stranded region that functions in RNA interference and a single stranded region that functions in antisense, wherein the double stranded region comprises a guide strand and a passenger strand, and wherein the double stranded region and the single stranded region are connected through a cleavable linker. In some embodiments, the cleavable linker includes one or more unmodified nucleotides. In other embodiments, the cleavable linker is a phosphodiester bond. In certain embodiments, the cleavable linker is S—S. In some embodiments the cleavable linker is DNA or RNA.

Aspects of the invention relate to methods for inhibiting the expression of a target gene in a mammalian cell, including contacting the mammalian cell with an isolated double stranded nucleic acid molecule comprising a guide strand and a passenger strand, wherein the passenger strand is connected through a cleavable linker to a single stranded region of at least eight phosphorothioate modified nucleotides. In some embodiments, the cleavable linker includes one or more unmodified nucleotides. In other embodiments, the cleavable linker is a phosphodiester bond. In certain embodiments, the cleavable linker is S—S. In some embodiments the cleavable linker is DNA or RNA.

The single stranded region comprises at least eight phosphorothioate modified nucleotides and can be at either the 3' or 5' end of the passenger strand. In some embodiments, the single stranded region of at least eight phosphorothioate modified nucleotides is DNA, while in other embodiments it is RNA. In some embodiments the double stranded region of the nucleic acid molecule is a perfect duplex. In other embodiments the double stranded region contains at least one bulge region. In some embodiments the passenger strand comprises a nick within the double stranded region of the molecule. The double stranded region may contain at least one nucleotide that is phosphorothioate modified.

The nucleic acid molecules associated with the invention may be chemically modified. In certain embodiments the chemical modification is 2'Omethyl and/or 2'Fluoro. In some embodiments more than one chemical modification is present in the same molecule. In some embodiments chemical modification increases stability, increases evasion of immune regulation, and/or prevents off-target gene silencing. Chemical modification can be present on the passenger strand and/or the guide strand.

In some embodiments the single stranded region of at least eight phosphorothioate modified nucleotides is cleaved from the double stranded region of the nucleic acid molecule in a cell. In some embodiments the single stranded region of at least eight phosphorothioate modified nucleotides has complementarity to a mammalian gene. In certain embodiments the single stranded region of at least eight phosphorothioate modified nucleotides functions as an antisense molecule. The double stranded region may be at least 19 nucleotides long. In some embodiments the single stranded region is at least 12 nucleotides long.

Aspects of the invention relate to methods for inhibiting the expression of a target gene in a mammalian cell, comprising contacting the mammalian cell with an isolated double stranded nucleic acid molecule comprising a guide strand and a passenger strand, wherein the guide strand is connected through a cleavable linker to a single stranded region of at least eight phosphorothioate modified nucleotides. In some embodiments, the cleavable linker includes one or more unmodified nucleotides. In other embodiments, the cleavable linker is a phosphodiester bond. In certain embodiments, the cleavable linker is S—S. In some embodiments the cleavable linker is DNA or RNA.

Aspects of the invention relate to methods for inhibiting the expression of a target gene in a mammalian cell, including contacting the mammalian cell with a bifunctional nucleic acid molecule including a double stranded region that functions in RNA interference and a single stranded region that functions in antisense, wherein the double stranded region includes a guide strand and a passenger strand, and wherein the double stranded region and the single stranded region are connected through a cleavable linker.

In other aspects a method for inhibiting the expression of a target gene in a mammalian cell is provided. The method involves contacting the mammalian cell with any of the isolated double stranded nucleic acid molecules described herein.

In some embodiments the isolated double stranded nucleic acid molecule includes a chemical modification that increases stability. In other embodiments the isolated double stranded nucleic acid molecule includes a chemical modification that increases evasion of immune regulation. In yet other embodiments the isolated double stranded nucleic acid molecule includes a chemical modification that prevents off-target gene silencing.

A method of inducing RNAi in a subject is provided in other aspects of the invention. The method involves administering to a subject an effective amount for inducing RNAi of an mRNA of a target gene any of the isolated double stranded nucleic acid molecules described herein. In some embodiments the subject is a human. In other embodiments the target gene may be PPIB, MAP4K4 or SOD1. In some embodiments the step of administering is systemic, intravenous, intraperitoneal, intradermal, topical, intranasal, inhalation, oral, intramucosal, local injection, subcutaneous, oral tracheal, or intraocular.

Use of an isolated double stranded nucleic acid molecule of the invention for inhibiting the expression of a target gene or treating a disease associated with expression of the target gene is also provided as an aspect of the invention.

A method for manufacturing a medicament of an isolated double stranded nucleic acid molecule of the invention for inhibiting the expression of a target gene or treating a disease associated with expression of the target gene is also provided.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2 is a schematic depicting several structural variations of the duplex moiety, in combination with different positioning of the phosphorothioate tail. The phosphorothioate tail can be positioned on the 3' or 5' end of the sense (or antisense) strand. In some embodiments, the double stranded region of the molecule is a perfect duplex, a duplex containing one or more bulges, or a duplex contain a nick in the sense strand. A variety of different chemical modifications can be applied to all of the potential structural variants of the molecules associated with the invention.

FIG. 10 is a table summarizing results obtained using nucleic acid constructs associated with the invention in experiments involving silencing of the PPIB gene.

FIG. 11 is a graph showing MAP4K4 expression in skin biopsies from mice injected intradermally with rxRNAs of different chemistries. The phosphorothioate tail was found to be necessary for cellular uptake and silencing activity in vivo.

DETAILED DESCRIPTION

Figure 1:
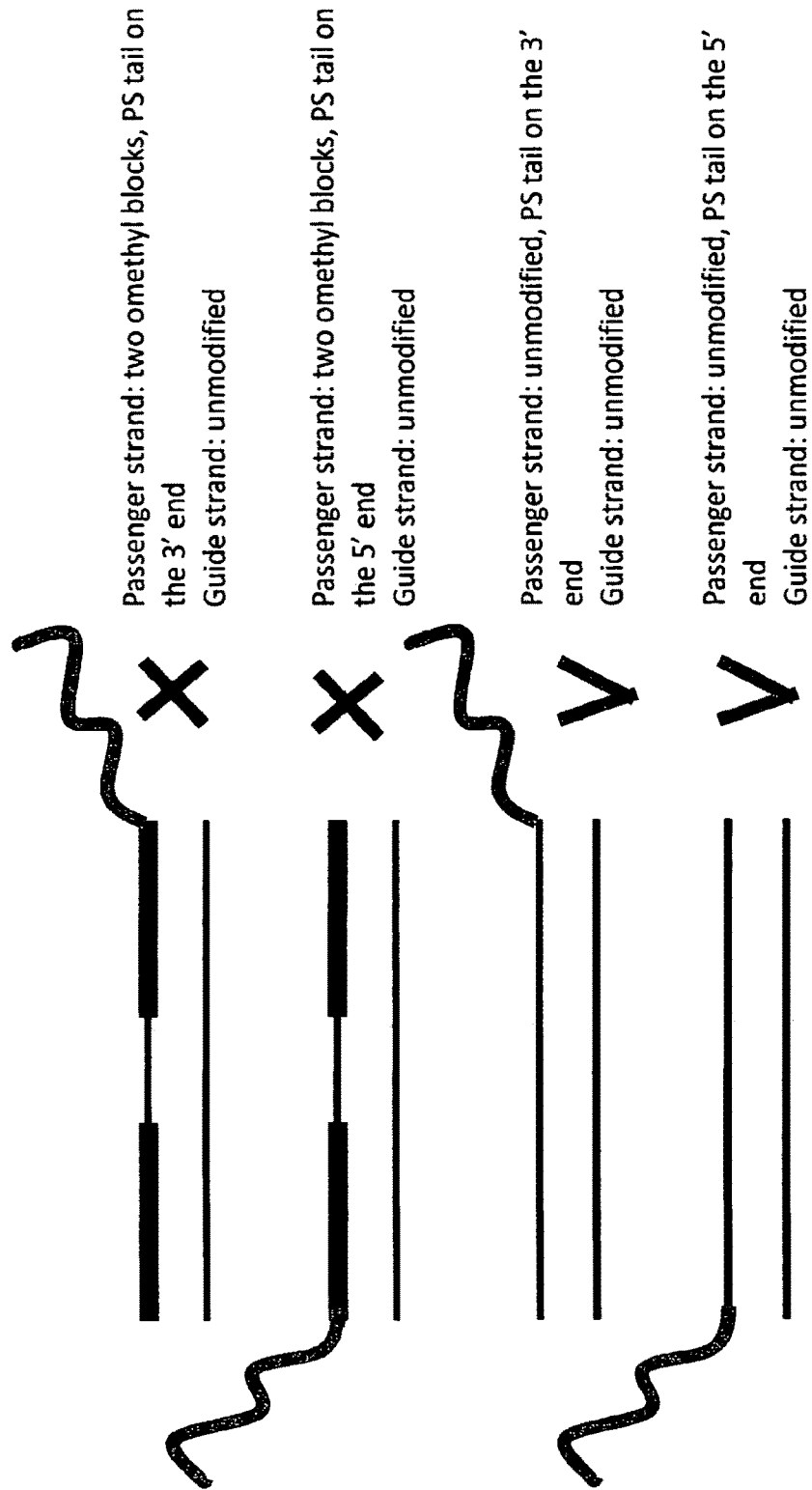
FIG. 1 is a schematic depicting RNAi constructs associated with the invention. When a phosphorothioate tail region was connected to the passenger (sense) strand, in combination with the presence of chemical modifications, cleavage of the tail was disrupted (indicated by an X). In the absence of chemical modifications, cleavage of the tail region was successful (indicated by a V)
Figure 3:
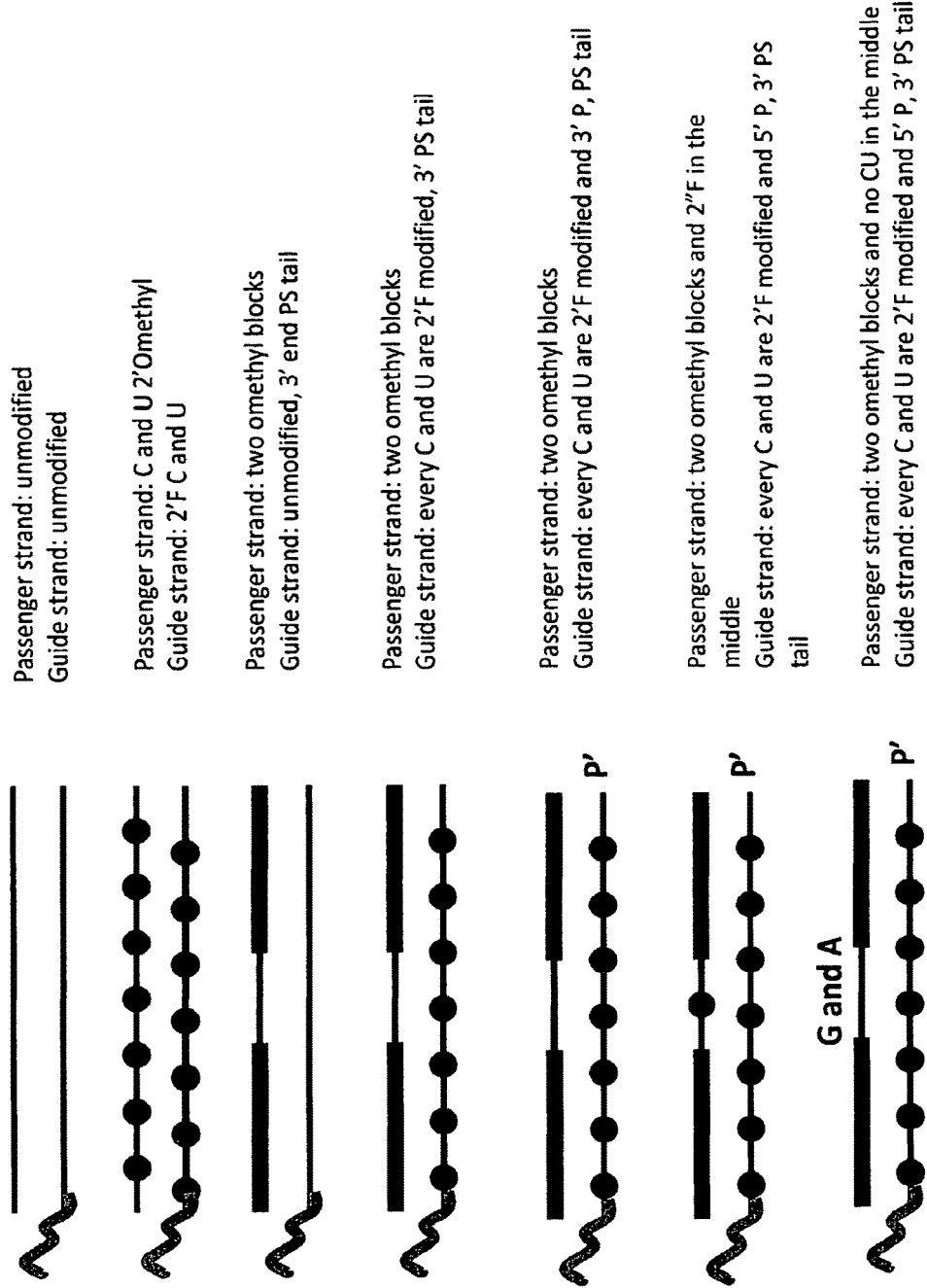
FIG. 3 is a schematic depicting different chemical modification patterns in combination with a phosphorothioate tail attached to the 3' end of the antisense strand. In some embodiments, when the phosphorothioate tail is attached to the antisense strand, the molecule can possess a wide variety of chemical modifications patterns, including combinations of different chemical modifications within the same molecule.
Figure 4:
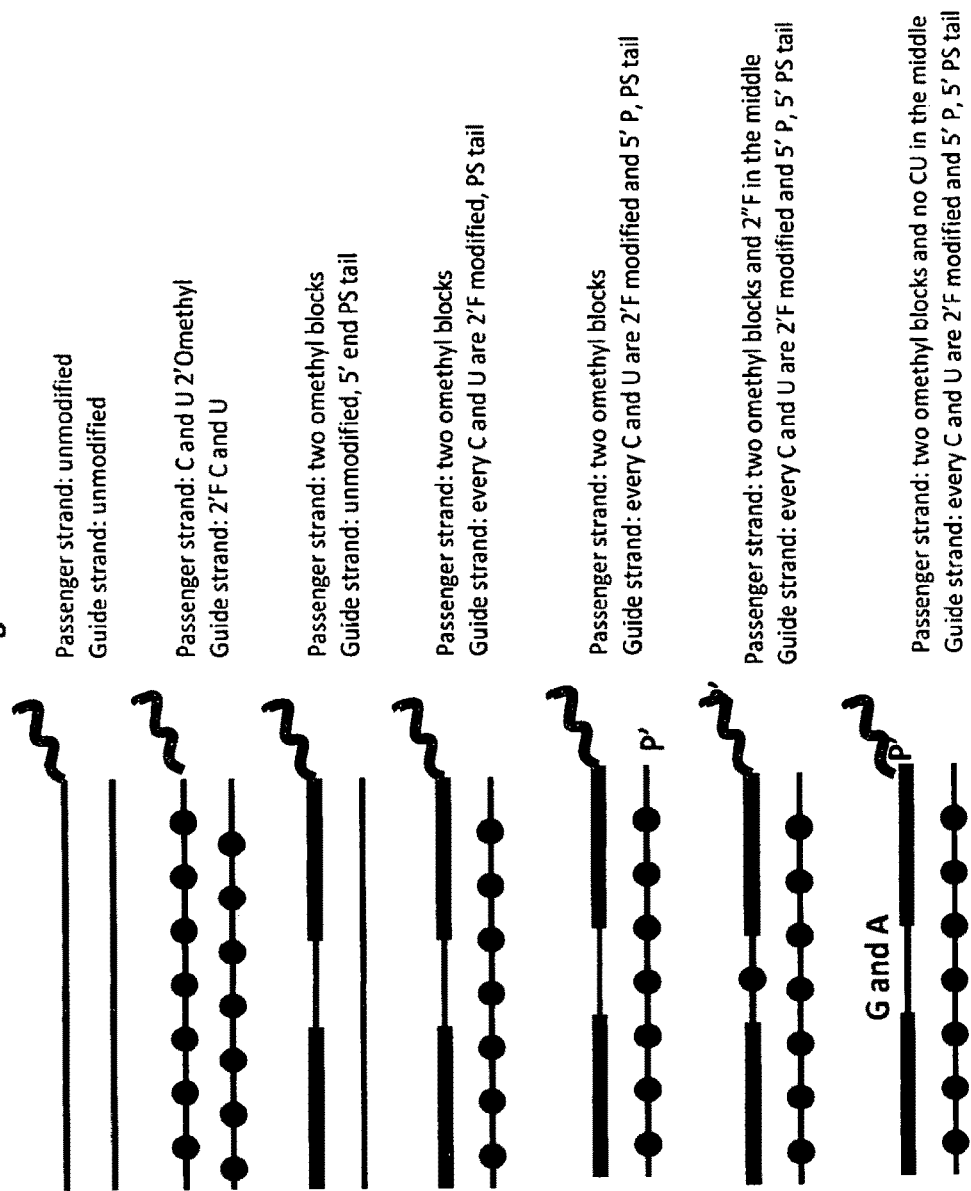
FIG. 4 is a schematic depicting different chemical modification patterns in combination with a phosphorothioate tail attached to the 5' end of the antisense strand.
Figure 5:
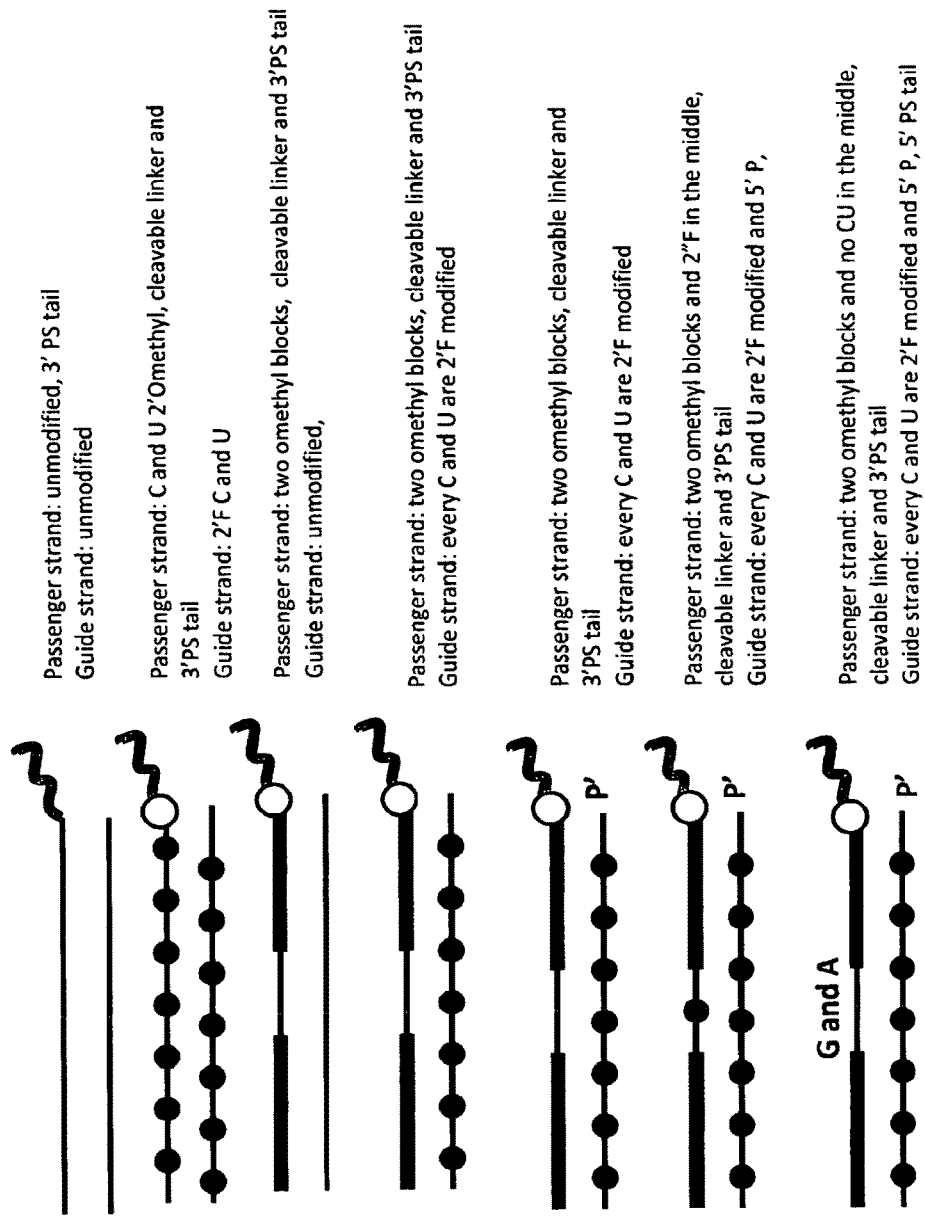
FIG. 5 is a schematic depicting different chemical modification patterns in combination with a phosphorothioate tail attached to the 3' end of the sense strand. In some embodiments, the phosphorothioate tail is connected through the cleavable linker region to the 3' end of the sense strand. In some embodiments the linker is a chemical linker (such as S—S). In other embodiments, the linker comprises one or more unmodified (or partially modified) nucleotides. In some embodiments, the phosphorothioate tail is passively removed during nucleolitic degradation or/and chemical reaction.
Figure 6:
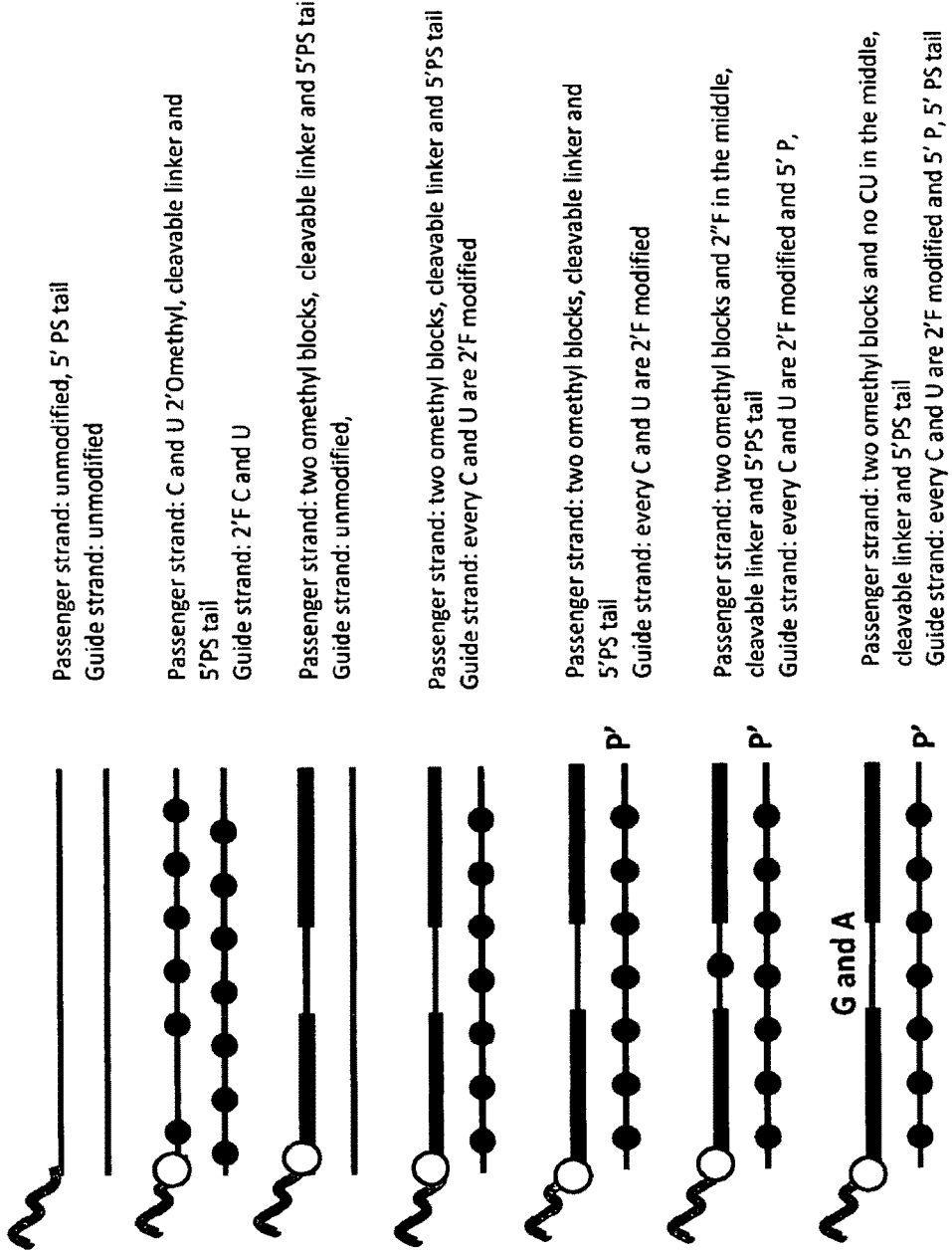
FIG. 6 is a schematic depicting different chemical modification patterns in combination with a phosphorothioate tail attached to the 5' end of the sense strand. In some embodiments, the phosphorothioate tail is connected through a cleavable linker region to the 5' end of the sense strand. In some embodiments the linker is a chemical linker (such as S—S). In other embodiments, the linker comprises one or more unmodified (or partially modified) nucleotides. In some embodiments, the phosphorothioate tail is passively removed during nucleolitic degradation or/and chemical reaction.
Figure 7:
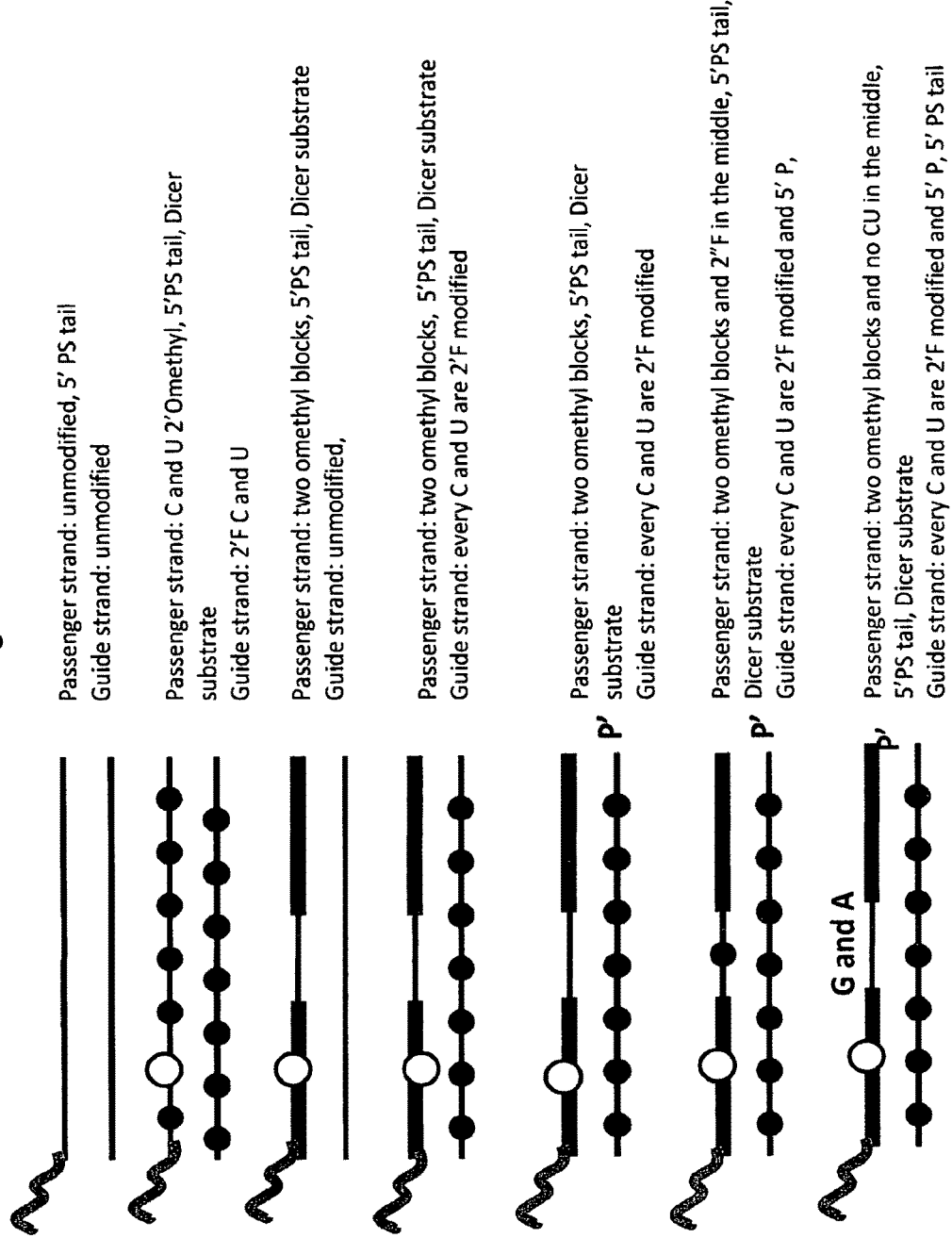
FIG. 7 is a schematic depicting different chemical modification patterns in combination with a phosphorothioate tail attached to the 5' end of the sense strand. In some embodiments, the molecule is modified such that it is a substrate for Dicer cleavage. As a result of Dicer processing, the phosphorothioate tail region is separated from the sense strand.
Figure 8:
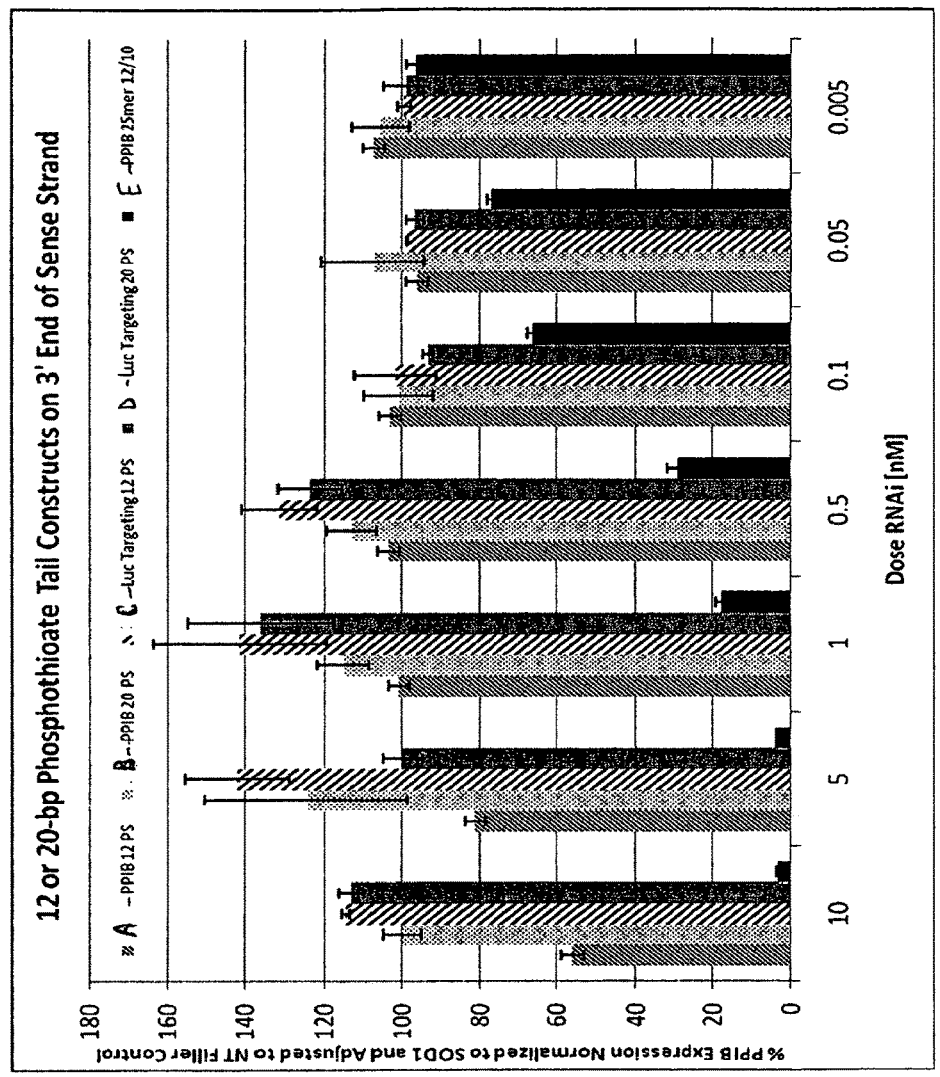
FIG. 8 is a graph demonstrating PPIB expression following transfection with nucleic acid constructs in which a 12 or 20 nucleotide phosphorothioate tail is attached to the 3' end of the sense strand. Constructs tested include: 12007-PPIB 12 PS, 12008-PPIB 20 PS, 12009-Luc Targeting 12 PS, 12010-Luc Targeting 20 PS and 11346-PPIB 25 mer 12/10.
Figure 9:
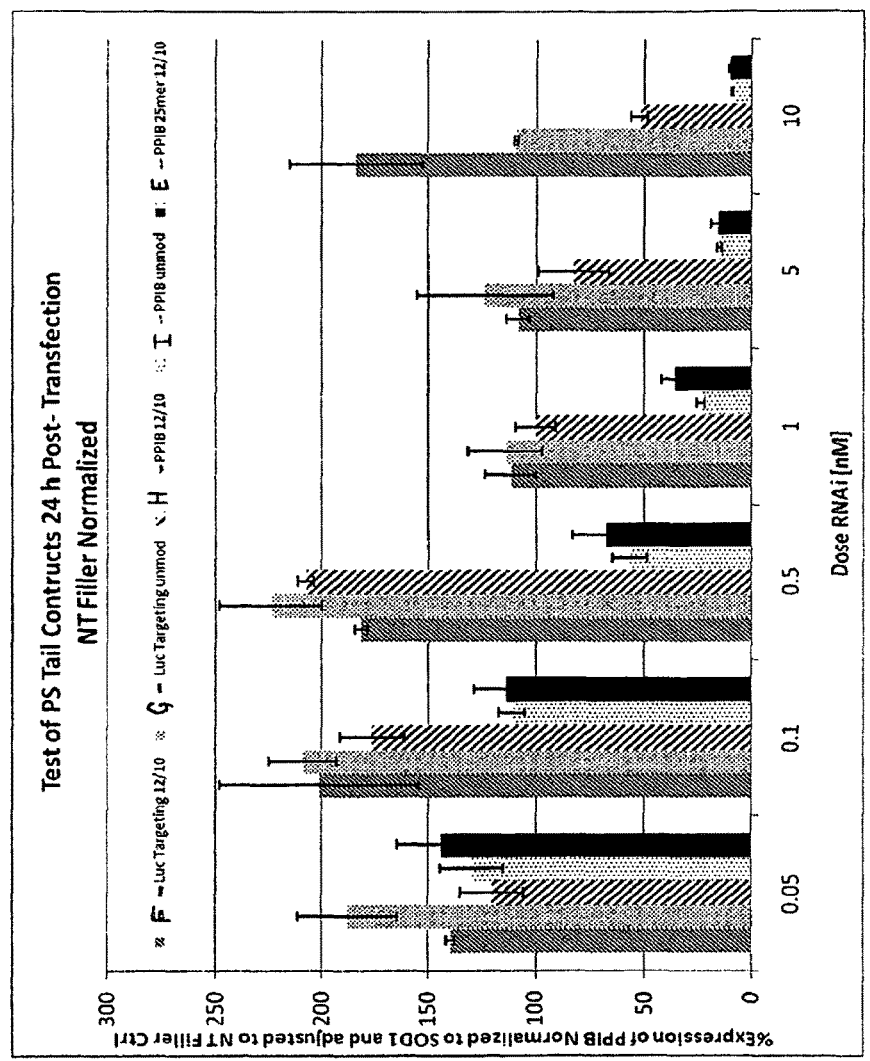
FIG. 9 is a graph demonstrating PPIB expression 24 hours post-transfection with nucleic acid constructs associated with the invention, including constructs in which a 12 nucleotide phosphorothioate tail is attached to the 5' end of the sense strand. Constructs tested include: 12203-Luc Targeting 12/10, 12204-Luc Targeting unmod, 12205-PPIB 12/10, 12206-PPIB unmod and 11346-PPIB 25 mer 12/10.

Aspects of the invention relate to methods and compositions involved in gene silencing. The invention relates at least in part to the development of RNAi constructs that contain, in addition to a double stranded region, a single stranded region of phosphorothioate modified nucleotides. Although not bound by any mechanism, it is believed that the single stranded region of the molecule assists in delivery of the molecule in vivo. Following delivery, the single stranded region is cleaved, allowing the double stranded region of the molecule to silence target gene expression. Also disclosed herein are novel bifunctional molecules comprising a double stranded region that optionally may function in mediating RNAi, and a single stranded region that functions in antisense regulation.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Previously, comparison of the properties of antisense oligonucleotides (e.g., single-stranded DNA or RNA, optionally including phosphorothioate modified backbones) with RNAi compounds (e.g., double-stranded RNA) had revealed a paradox. In cell culture studies involving transfection, using transfection reagents such as Lipofectin (Invitrogen, Carlsbad, Calif.), antisense compounds have been observed to have effective concentrations demonstrating $EC_{50}$ values of 1-20 nM (Antisense Drug Technology: Principles, Strategies, and Applications, by Stanley T. Crooke (Editor) Publisher: CRC; 2nd edition, 2007), whereas optimized RNAi compounds have been observed to demonstrate $EC_{50}$ values of approximately 5-50 pM. However, in animal studies, antisense phosphorothioate compounds have been observed to be active at an effective dose causing 50% inhibition ($ED_{50}$) of approximately 1 mg/kg, whereas RNAi compounds have been observed to be active at an $ED_{50}$ of >50 mg/kg.

This difference in pharmacological properties cannot be attributed simply to a difference in RNA vs. DNA. While antisense is frequently associated with DNA, and RNAi with RNA, in fact antisense molecules with favorable pharmacological properties frequently comprise at least 50% modified RNA nucleotides (Antisense Drug Technology: Principles, Strategies, and Applications, by Stanley T. Crooke (Editor) Publisher: CRC; 2nd edition, 2007). Furthermore, the difference in pharmacological properties cannot be attributed simply to a difference in single-stranded vs. double-stranded molecules because single-stranded RNA drugs such as ribozymes and aptamers, with primarily phosphodiester backbones, have also been observed to exhibit poor pharmacological properties similar to that of RNAi molecules. Additionally, simply adding phosphorothioate linkages to RNAi compounds has not been successful in making the pharmacology of RNAi as favorable as antisense.

Surprisingly, results described herein suggest that the properties of a nucleic acid molecule can be manipulated by adding a stretch of single-stranded phosphorothiote-modified nucleotides (e.g., >8 nucleotides) to the nucleic acid molecule. Specifically, a stretch of phosphorothioate-modified single-stranded nucleotides can impart favorable antisense pharmacology to RNAi compounds. Methods and compositions associated with the invention exploit this phenomenon to design RNAi compounds that have favorable pharmacological properties of antisense molecules, but also the higher intrinsic (cellular) activity of RNAi molecules.

Antisense compounds that have approximately 8 or more phosphorothioate linkages (e.g., >12, or >14) are known to bind to many proteins including serum albumin. Without wishing to be bound by any theory, serum albumin binding has been associated with longer serum half-lives of antisense molecules, allowing such molecules to distribute to various tissues such as liver, bone marrow, adipocytes, spleen, intestine and others. It has also been hypothesized that the general affinity of antisense phosphorothioates for proteins enhances endocytosis and enoplasmic release by a protein shuttling mechanism. (Antisense Drug Technology: Principles, Strategies, and Applications, by Stanley T. Crooke (Editor) Publisher: CRC; 2nd edition, 2007).

Methods and compositions described herein involve nucleic acid molecules in which phosphorothioate modified nucleotides are located at least in part within a single-stranded region of a nucleic acid molecule. While not bound by any theory, placement of phosphorothioate linkages within conformationally flexible single-stranded regions may allow the phosphorothioate linkage to form cooperative interactions which may be more difficult to form when the phosphorothioate linkage is located within a relatively conformationally rigid form of dsRNA (e.g., RNAi compounds).

RNAi compounds described herein have improved pharmacological properties through incorporation of stretches of single-stranded phosphorothioate linkages. Surprisingly, single-stranded phosphorothioate regions can in some instances reduce RNA interference when transfected into a cell (e.g., by cationic lipids). Aspects of the invention relate to compounds in which the phosphorothioate region is released within a cell from the dsRNA region of the compound, thus liberating the fully active RNAi compound with the cytoplasm.

Conformational flexibility of incorporated phosphorothioate linkages does not require that all such linkages be in single-stranded regions; some or all of the phosphorothioate linkages can be in double-stranded regions. In some embodiments, a flexible region which interrupts the otherwise more rigid duplex in the RNAi compound may be inserted (e.g., by placing a mismatched bulge in the central region of a duplex).

Previous attempts to add large numbers of phosphorothioate linkages to RNAi molecules have been hindered by a reduction in the intrinsic RNAi activity of compounds with more than 5 or 10 phosphorothioate linkages. In some embodiments, aspects of the invention provide for configurations in which the phosphorothioate linkages are in different regions of the RNA molecule (e.g., tail or loop) to mitigate this effect.

The double stranded nucleic acid molecules of the invention have one or more nucleotides with phosphorothioate (PS) internucleotide linkages. DNA with a phosphorothioate backbone structure has been used for the delivery of antisense DNA nucleotides to various tissues in the body without the requirement of additional formulation (Antisense Drug Technology: Principles, Strategies, and Applications, by Stanley T. Crooke (Editor) Publisher: CRC; 2nd edition, 2007). However, less success has been reported for using such phosphorothioate backbone structures in siRNAs for in vivo delivery. Described herein is a strategy for delivering double stranded RNAi compounds to cells or tissues in the body through the addition of a phosphorothioate tail sequence. As used herein, a "phosphorothioate tail" or a "PS tail" refers to a single-stranded region of nucleotides that are fully or partially phosphorothioate modified. The PS tail region can be DNA or RNA or a chimeric mixture of RNA and DNA. In some embodiments the PS tail region contains one or more chemical modifications. The PS tail can contain any modification known in the art such as 2'-X or 2'-O—X, wherein X can be any modification known in the art (e.g., 2'-O-methyl, 2'-fluoro, 2'-propyl, propenyl etc.). The PS tail can also contain LNA. In some embodiments, the PS tail can be phosphorodithioate, potentially allowing for shorter tail lengths. The PS tail can also be abasic, or other compounds with "sticky" sulphur linkages, such as heparin sulfphate.

The PS tail can be 3 nucleotides or more. For example, the PS tail can be 3, 4, 5, 6, 7, 8, 9, 10, 11, 12, 13, 14, 15, 16, 17, 18, 19, 20, 21, 22, 23, 24, 25 or more than 25 nucleotides. In some embodiments the PS tail region is greater than or equal to 12 nucleotides. In some embodiments the PS tail is a maximum length of 100 nucleotides. In other embodiments the PS tail is a maximum length of 30, 35, 40, 45, 50, 60, or 75 nucleotides. In some embodiments the PS tail region is attached to the antisense (guide) strand of an RNA duplex molecule. In other embodiments the PS tail region is attached to the sense (passenger) strand of an RNA duplex molecule. In some embodiments the PS tail is attached to the 3' end of either or both the sense or antisense strand of an RNA duplex molecule. In other embodiments the PS tail is attached to the 5' end of either or both the sense or antisense strand of an RNA duplex molecule. If the PS tail is on the antisense strand, it is sometimes preferable to attach it to the 3' end of the antisense strand because the 5' end of the antisense strand may be involved in targeting of the molecule. In certain embodiments the PS tail is at the 3' end of the antisense strand. In some embodiments, the 5' end of the sense strand is preferred for conjugation or attachment of the PS tail through incorporation of the tail during the RNAi solid phase synthesis.

In some embodiments the stretch of nucleotides that is phosphorothioate modified includes the single stranded stretch of nucleotides and also includes one or more of the double stranded nucleotides. Thus, in some embodiments one or more of the double stranded nucleotides in an RNAi molecule is phosphorothioate modified. Phosphorothioate modified resides can be located in any portion of a nucleic acid molecule described herein such as in a loop or hairpin, a bulge of a soloRNA or a bulge of an siRNA.

The RNA duplex region may be any length that is appropriate for mediating RNAi. For instance, it may be at least 19 nucleotides, or in some instances it may be less than 19 nucleotides long. In some embodiments the duplex can be 12 nucleotides or longer. For example the RNA duplex region can be between 12-30, 19-30, 12-40, 19-40, 12-50, 19-50, 12-70, 19-70, 12-100 or 19-100 nucleotides long. The nucleic acid molecule can also comprise two or more separate duplex regions such as two separate 12 nucleotide duplexes. The guide strand of the RNA duplex region has complementarity to a target gene. Complementarity between the guide strand and the target gene may exist over any portion of the guide strand. Complementarity as used herein may be perfect complementarity or less than perfect complementarity as long as the guide strand is sufficiently complementary to the target that it mediates RNAi. In some embodiments complementarity refers to less than 25%, 20%, 15%, 10%, 5%, 4%, 3%, 2%, or 1% mismatch between the guide strand and the target. The passenger strand of the RNA duplex has complementarity to the guide strand. Complementarity between the passenger strand and the guide strand can exist over any portion of the passenger or guide strand. In some embodiments, there is 100% complementarity between the guide and passenger strands within the double stranded region of the molecule. In some embodiments, there is less than 100% complementarity between the guide and passenger strands within the double stranded region of the molecule.

In some embodiments it is preferred that the single stranded tail is connected to the guide strand.

RNA molecules associated with the invention and having a phosphorothioate tail can have basic structure of other RNA molecules. For instance, some RNA molecules are double stranded RNA, each strand having 19-25 nucleotides, and optionally 2 3' overhangs.

The RNA molecules can also be sd ("self-delivering")-rxRNA$^{nano}$ molecules. Such molecules can also be referred to as "nano RNA" or "sd-rxRNA." As used herein, "sd-rxRNA$^{nano}$" molecules are asymmetric chemically modified nucleic acid molecules with double-stranded regions of minimal length such as 8-14 nucleotides. These and other RNAi molecules associated with the invention can contain a variety of chemical modifications on the sense and/or antisense strand and can also be attached to a hydrophobic conjugate such as conventional and advanced sterol-type molecules.

An sd-rxRNA$^{nano}$ molecule can in some aspects includes a guide strand with a minimal length of 16 nucleotides, and a passenger strand, forming a double stranded nucleic acid, having a double stranded region and a single stranded region, the double stranded region having 8-15 nucleotides in length, the single stranded region having 5-12 nucleotides in length, wherein the passenger strand is linked to a lipophilic group, wherein at least 40% of the nucleotides of the double stranded nucleic acid are modified. Position 1 of the guide strand can be 5' phosphorylated and in some embodiments is also 2'O-methyl modified.

An sd-rxRNA$^{nano}$ molecule can in some aspects include a guide strand of 17-21 nucleotides in length that has complementarity to a target gene and a passenger strand of 8-16 nucleotides in length linked at the 3' end to a lipophilic group. The guide strand can have a 3' single stranded region of 3-13 nucleotides in length. The guide strand of such molecules can also be 5' phosphate modified and can contain at least one 2' O-methyl modification or 2'-fluoro modification of one or more C and/or U nucleotides in the double stranded region. The passenger (sense) strand can also contain modifications such as the addition of methyl groups.

Further description of sd-rxRNA$^{nano}$ molecules is incorporated by reference from U.S. Provisional Application No. 61/192,954, entitled "Chemically Modified Polynucleotide's and Methods of Using the Same," filed on Sep. 22, 2008, U.S. Provisional Application No. 61/149,946, entitled "Minimum Length Triggers of RNA Interference," filed on Feb. 4, 2009, U.S. Provisional Application No. 61/224,031, entitled "Minimum Length Triggers of RNA Interference," filed on Jul. 8, 2009, and PCT Application No. PCT/US2009/005247, entitled "Reduced Size Self-Delivering RNAi Compounds," filed on Sep. 22, 2009, the disclosure of each of which is incorporated by reference herein in its entirety.

While not wishing to be bound by any particular theory, results described herein suggest that a single-stranded PS tail region partially inhibits the RNAi activity of a double stranded (duplex) region of an RNAi construct. Once the single stranded PS tail region is cleaved from the duplex region in the cell, the duplex region can silence the expression of target genes. In some embodiments, if the RNA duplex is long enough to be a Dicer substrate (for example approximately 25 nucleotides) and chemically modified such that Dicer processing is blocked, the PS tail inhibits the silencing activity of the RNAi portion of the molecule. In some embodiments, an unmodified duplex with a PS tail, that is cleaved by Dicer, is active.

In some embodiments, the single stranded PS tail region of the molecule is designed with sequence characteristics such that it will silence a nuclear gene by an antisense mechanism. Thus, aspects of the invention relate to bifunctional nucleic acid molecules comprising a double stranded region that functions in RNA interference and a single stranded region that functions in antisense regulation. In some embodiments, the PS tail portion of the molecule is cleaved from the duplex region in the cytoplasm and travels to the nucleus. In some embodiments, the duplex portion of the molecule remains in the cytoplasm and silences genes by cleaving target mRNA by an RNAi based mechanism. In some embodiments the bi-functional molecule targets the same gene by two different mechanisms for an increase in potency. In other embodiments, the bi-functional molecule targets two different genes.

An advantage of the bifunctional molecules described herein is the opportunity for synergistic inhibition of gene expression. While not being bound by any theory, the mechanism of antisense acts in the nucleus and cleaves a proportion of the targets by RNase H. The reduced amount of mRNA that reaches the cytoplasm would then be cleaved by the RNAi mechanism which primarily acts in the cytoplasm. For example, an approximate 90% reduction in gene expression achieved by antisense, in conjunction with an approximate 90% reduction in gene expression achieved by RNAi, could lead to an approximate 99%-100%, or almost complete reduction in gene expression.

The phosphorothioate tail may be directly or indirectly connected to the RNA duplex through the use of a cleavable linker. A phosphorothioate tail that is directly connected to the RNA duplex through a cleavable linker includes the RNA duplex linked to the tail through the cleavable linker. A phosphorothioate tail that is indirectly connected to the RNA duplex through a cleavable linker includes one ore more additional molecules such as nucleotides between the RNA duplex and the cleavable linker and/or the tail.

Cleavable linker regions may be used to join the double stranded duplex region of an RNA molecule to a single stranded PS tail region. A cleavable linker is one or more molecules or bonds that connect two or more components of the molecule and is susceptible to cleavage under appropriate conditions. For instance, the appropriate conditions may be the conditions within a cell. For instance, the cleavable linker may be one or more nucleotides, which preferably are unmodified or if modified are susceptible to cleavage under the appropriate conditions. The nucleotides may be labile nucleotides. In some embodiments one or more of the nucleotides in the double stranded region adjacent to the single stranded region are unmodified. In certain embodiments 1, 2, 3, 4, 5, or more than 5 of the nucleotides in the double stranded region immediately adjacent to the single stranded region are unmodified. The nucleotides in the cleavable linker may be DNA or RNA or a chimeric DNA-RNA region. The cleavable linker may be a bond between the RNA duplex and the tail, such as a phosphodiester bond. In some embodiments the cleavable linker region comprises a chemical linker such as S—S (phosphorothioate-phosphorothioate).

The linker between the double stranded and single stranded regions of the molecule may be a modified internucleoside linkage, preferably one that is cleavable. As used herein, "modified internucleoside linkage" and "modified backbone," or simply "modified linkage," refer to modifications or replacement of the naturally occurring phosphodiester internucleoside linkage connecting two adjacent nucleosides within an oligomeric compound. Such modified linkages include those that have a phosphorus atom and those that do not have a phosphorus atom.

Internucleoside linkages containing a phosphorus atom therein include, for example, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage, as long as the linkage is susceptible to cleavage in the context of the nucleic acid. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697, 5,625,050 and 5,697,248 the entire contents of which are incorporated herein by reference.

Another phosphorus containing modified internucleoside linkage is the phosphonomonoester (see U.S. Pat. Nos. 5,874,553 and 6,127,346, the entire contents of which are incorporated herein by reference). Phosphonomonoester nucleic acids have useful physical, biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

An oligonucleoside refers to a sequence of nucleosides that are joined by internucleoside linkages that do not have phosphorus atoms. Non-phosphorus containing internucleoside linkages include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the entire contents of which are incorporated herein by reference.

Some additional examples of modified internucleoside linkages that do not contain a phosphorus atom therein include, —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(O)(OH)—O—$CH_2$—). The MMI type and amide internucleoside linkages are disclosed in the below referenced U.S. Pat. Nos. 5,489,677 and 5,602,240, respectively, the entire contents of which is incorporated herein by reference.

The linkers may be non-nucleotide in nature. Non-nucleotidic linkers are e.g. abasic residues (dSpacer), oligoethyleneglycol, such as triethyleneglycol (spacer 9) or hexaethylenegylcol (spacer 18), or alkane-diol, such as butanediol. The spacer units are preferably linked by phosphodiester or phosphorothioate bonds. The linker units may appear just once in the molecule or may be incorporated several times, e.g. via phosphodiester, phosphorothioate, methylphosphonate, or amide linkages. Further preferred linkers are alkylamino linkers, such as C3, C6, C12 aminolinkers, and also alkylthiol linkers, such as C3 or C6 thiol linkers. The nucleic acids can also be linked by aromatic residues which may be further substituted by alkyl or substituted alkyl groups. The nucleic acids may also contain a Doubler or Trebler unit, which allow conjugation of multiple ligands of one or different types to the nucleic acids. The nucleic acids may also contain linker units resulting from peptide modifying reagents or nucleic acid modifying reagents (www.glenres.com). Furthermore, it may contain one or more natural or unnatural amino acid residues which are connected by peptide (amide) linkages. Different types of linkers may also be combined to new linkers.

In yet another embodiment, a non-nucleotide linker of the invention comprises abasic nucleotide, polyether, polyamine, polyamide, peptide, carbohydrate, lipid, polyhydrocarbon, or other polymeric compounds (e.g. polyethylene glycols such as those having between 2 and 100 ethylene glycol units). Specific examples include those described by Seela and Kaiser, Nucleic Acids Res. 1990, 18:6353 and Nucleic Acids Res. 1987, 15:3113; Cload and Schepartz, J. Am. Chem. Soc. 1991, 113:6324; Richardson and Schepartz, J. Am. Chem. Soc. 1991, 113:5109; Ma et al., Nucleic Acids Res. 1993, 21:2585 and Biochemistry 1993, 32:1751; Durand et al., Nucleic Acids Res. 1990, 18:6353; McCurdy et al., Nucleosides & Nucleotides 1991, 10:287; Jschke et al., Tetrahedron Lett. 1993, 34:301; Ono et al., Biochemistry 1991, 30:9914; Arnold et al., International Publication No. WO 89/02439; Usman et al., International Publication No. WO 95/06731; Dudycz et al., International Publication No. WO 95/11910 and Ferentz and Verdine, J. Am. Chem. Soc. 1991, 113:4000, all hereby incorporated by reference herein. A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

Photo-crosslinking agents include aryl azides such as, for example, N-hydroxysucciniimidyl-4-azidobenzoate (HSAB) and N-succinimidyl-6(-4'-azido-2'-nitrophenyl-amino)hexanoate (SANPAH). Aryl azides conjugated to oligonucleotides effect crosslinking with nucleic acids and proteins upon irradiation, They also crosslink with carrier proteins (such as KLH or BSA), raising antibody against the oligonucleotides.

A variety of linking groups can be used to connect the substituents of the invention to nucleosides, nucleotides, and/or oligonucleotides. Certain linking groups, such as .OMEGA.-aminoalkoxy moieties and .OMEGA.-aminoalkylamino moieties, are particularly useful for linking steroid molecules or reporter molecules to the T-position of a nucleoside. Many linking groups are commercially available, including heterobifunctional and homobifunctional linking moieties available from the Pierce Co. (Rockford, Ill.). Heterobifunctional and homobifunctional linking moieties are particularly useful in conjunction with the .OMEGA.-aminoalkoxy and .OMEGA.-aminoalkylamino moieties to form extended linkers that connect peptides and proteins to nucleosides. Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.). A nucleotide analog bearing a linking group pre-attached to the nucleoside is commercially available from Glen Research Corporation under the tradename "Amino-Modifier-dT." This nucleoside-linking group reagent, a uridine derivative having an [N(7-trifluoroacetylaminoheptyl)3-acrylamido] substituent group at the 5 position of the pyrimidine ring, is synthesized generally according to Jablonski, et al., Nucleic Acid Research 1986, 14, 6115. It is intended that the nucleoside analogs of the invention include adenine nucleosides functionalized with linkers on their N6 purine amino groups, guanine nucleosides functionalized with linkers at their exocyclic N2 purine amino groups, and cytosine nucleosides functionalized with linkers on either their N4 pyrimidine amino groups or 5 pyrimidine positions.

The different nucleic acids are synthesized by established methods and can be linked together on-line during solid-phase synthesis. Alternatively, they may be linked together post-synthesis of the individual partial sequences.

The cleavable linker region may be incorporated into the nucleic acid during nucleic acid synthesis. Alternatively it may be added chemically to the components, depending on the nature of the cleavable linker.

The PS tail may be cleaved from the duplex region of the RNA molecule through passive cleavage. In some embodiments passive cleavage is achieved through the addition of one or more nucleotides that are not phosphorothioate modified immediately adjacent to the attachment to the duplex. For example, 1, 2, 3, 4, 5, or more than 5 nucleotides that are not phosphorothioate modified may be added. In some embodiments the one or more nucleotides that are not phosphorothioate modified are within the single stranded tail portion of the molecule. In other embodiments, the one or more nucleotides that are not phosphorothioate modified are within the duplex region of the molecule. The one or more nucleotides can be RNA or DNA. In some embodiments DNA is preferred because single stranded RNA is more sensitive to serum nucleases than single stranded DNA, while single stranded DNA is rapidly degraded by cellular nucleases. In some embodiments cleavage occurs through processing by an RNase molecule. In some embodiments cleavage occurs through a chemical reaction. Without wishing to be bound by any theory, a linker associated with the invention may be a pH sensitive linker. In some instances, entry of an RNA construct into an endosome within a cell may lead to cleavage of the PS tail due to the low pH conditions within the endosome. The tail could be conjugated by one of any number of linkages which is unstable in the cytoplasm, For example, in some embodiments a disulphide bond may be stable outside of the cell and in endosomes, but may be oxidized inside the cytoplasm. Furthermore the phosphorothioate region can be bound to the RNAi compound by hybridization, wherein the off rate is sufficient to melt over time within the cell.

In some embodiments the nucleic acid molecules of the invention are chemically modified. Some non-limiting examples of modifications include 2'Omethyl and 2'Fluoro modifications. Modifications to nucleic acid molecules and cleavage of such molecules are discussed further in U.S. Provisional Application No. 61/135,855, entitled "Short Hairpin RNAi Constructs and Uses Thereof," filed on Jul. 24, 2008, the entire contents of which is incorporated herein by reference. In some embodiments, modification of the nucleic acid molecule achieves beneficial therapeutic properties such as stability, evasion of immune regulation and prevention of off-target effects. In some embodiments, chemical modification of the nucleic acid molecule improves for in vivo efficacy. It should be appreciated that a nucleic acid molecule can include more than one chemical modification. A wide variety of modifications on either the sense or antisense strand can be associated with the molecules of the invention.

It should be appreciated that a PS tail region as described herein can be added to any nucleic acid molecule. In some embodiments the nucleic acid molecule is a miniRNA or a soloRNA discussed further in application U.S. Provisional Application No. 61/197,768, entitled "miniRNA Constructs and Uses Thereof," filed on Oct. 30, 2008, the entire contents of which is incorporated herein by reference. In some embodiments the nucleic acid molecule is a minimum trigger RNAi molecule discussed further in copending application "Minimum Length Triggers of RNA Interference," filed concurrently herewith, the entire contents of which is incorporated herein by reference.

Duplex Characteristics

Double-stranded oligonucleotides of the invention may be formed by two separate complementary nucleic acid strands. Duplex formation can occur either inside or outside the cell containing the target gene.

As used herein, the term "double-stranded" includes one or more nucleic acid molecules comprising a region of the molecule in which at least a portion of the nucleomonomers are complementary and hydrogen bond to form a duplex.

As used herein, the term "duplex" includes the region of the double-stranded nucleic acid molecule(s) that is (are) hydrogen bonded to a complementary sequence. Double-stranded oligonucleotides of the invention may comprise a nucleotide sequence that is sense to a target gene and a complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

In certain embodiments, the double-stranded oligonucleotide of the invention is double-stranded over its entire length, i.e., with no overhanging single-stranded sequence at either end of the molecule, i.e., is blunt-ended. In other embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

In one embodiment, a double-stranded oligonucleotide of the invention contains mismatches and/or loops or bulges, but is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide. In certain embodiments, the double-stranded oligonucleotide of the invention contains at least or up to 1, 2, 3, 4, 5, 6, 7, 8, 9, 10, 11, 12, 13, 14, or 15 mismatches.

Modifications

The nucleotides of the invention may be modified at various locations, including the sugar moiety, the phosphodiester linkage, and/or the base.

Sugar moieties include natural, unmodified sugars, e.g., monosaccharide (such as pentose, e.g., ribose, deoxyribose), modified sugars and sugar analogs. In general, possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like.

One particularly useful group of modified nucleomonomers are 2'-O-methyl nucleotides. Such 2'-O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a non-naturally occurring base (instead of a naturally occurring base), such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alxoxy (or OR), R or alkyl, halogen, SH, SR, amino (such as $NH_2$, NHR, $NR_2$), or CN group, wherein R is lower alkyl, alkenyl, or alkynyl.

Modified ribonucleotides may also have the phosphoester group connecting to adjacent ribonucleotides replaced by a modified group, e.g., of phosphorothioate group. More generally, the various nucleotide modifications may be combined.

Although the antisense (guide) strand may be substantially identical to at least a portion of the target gene (or genes and complementary to the target transcript), at least with respect to the base pairing properties, the sequence need not be perfectly identical to be useful, e.g., to inhibit expression of a target gene's phenotype. Generally, higher homology can be used to compensate for the use of a shorter antisense gene. In some cases, the antisense strand generally will be substantially identical (although in antisense orientation) to the target gene.

The use of 2'-O-methyl modified RNA may also be beneficial in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This may be useful, for example, for avoiding the interferon or other cellular stress responses, both in short RNAi (e.g., siRNA) sequences that induce the interferon response, and in longer RNAi sequences that may induce the interferon response.

Overall, modified sugars may include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy ($—OCH_2CH=CH_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902, incorporated by reference herein.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O⁻ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-2}R'$, $(CR'R'')_{0-3}O(CR'R'')_{0-3}H$, $(CR'R'')_{0-3}COR'$, $(CR'R'')_{0-3}CO_2R'$, or $(CR'R'')_{0-3}OR'$ groups; wherein each R' and R" are each independently hydrogen, a $C_1$-$C_5$ alkyl, $C_2$-$C_5$ alkenyl, $C_2$-$C_5$ alkynyl, or aryl group, or R' and R" taken together are a benzylidene group or a —$(CH_2)_2O(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligonucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", 2$^{nd}$ Ed., Wiley-Interscience, New York, 1999).

The term "nucleotide" includes nucleosides which further comprise a phosphate group or a phosphate analog.

As used herein, the term "linkage" includes a naturally occurring, unmodified phosphodiester moiety (—O—$(PO^{2-})$—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolizable linkages are preferred, such as phosphorothioate linkages.

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—$CH_2$—$CH_2$—O—) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. Antisense Res. Dev. 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3'linked nucleotide at the 3' terminus can be linked by a substitute linkage. To reduce nuclease degradation, the 5' most linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

Another type of conjugates that can be attached to the end (3' or 5' end), the loop region, or any other parts of the miniRNA might include a sterol, sterol type molecule, peptide, small molecule, protein, etc. In some embodiments, a miniRNA may contain more than one conjugates (same or different chemical nature). In some embodiments, the conjugate is cholesterol.

Another way to increase target gene specificity, or to reduce off-target silencing effect, is to introduce a 2'-modification (such as the 2'-O methyl modification) at a position corresponding to the second 5'-end nucleotide of the guide sequence. This allows the positioning of this 2'-modification in the Dicer-resistant hairpin structure, thus enabling one to design better RNAi constructs with less or no off-target silencing.

In one embodiment, a hairpin polynucleotide of the invention can comprise one nucleic acid portion which is DNA and one nucleic acid portion which is RNA. Antisense (guide) sequences of the invention can be "chimeric oligonucleotides" which comprise an RNA-like and a DNA-like region.

The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

In one embodiment, at least a portion of the contiguous polynucleotides are linked by a substitute linkage, e.g., a phosphorothioate linkage.

In certain embodiments, most or all of the nucleotides beyond the guide sequence (2'-modified or not) are linked by phosphorothioate linkages. Such constructs tend to have improved pharmacokinetics due to their higher affinity for serum proteins. The phosphorothioate linkages in the non-guide sequence portion of the polynucleotide generally do not interfere with guide strand activity, once the latter is loaded into RISC.

Antisense (guide) sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate inter-subunit linkages. Morpholino oligonucleotides have many advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl. Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

Synthesis

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art).

In a preferred embodiment, chemical synthesis is used for modified polynucleotides. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. J. Am. Chem. Soc. 106:6077; Stec et al. 1985. J. Org. Chem. 50:3908; Stec et al. J. Chromatog. 1985. 326:263; LaPlanche et al. 1986. Nucl. Acid. Res. 1986. 14:9081; Fasman G. D., 1989. Practical Handbook of Biochemistry and Molecular Biology. 1989. CRC Press, Boca Raton, Fla.; Lamone. 1993. Biochem. Soc. Trans. 21:1; U.S. Pat. Nos. 5,013,830; 5,214,135; 5,525,719; Kawasaki et al. 1993. J. Med. Chem. 36:831; WO 92/03568; U.S. Pat. Nos. 5,276,019; and 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, Chemical Reviews 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. Methods in Molecular Biology 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, J Am. Chem. Soc. 104:976; Viari, et al., 1987, Biomed. Environ.

*Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. *J Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (D N Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

Delivery/Carrier

Uptake of Oligonucleotides by Cells

Oligonucleotides and oligonucleotide compositions are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In a preferred embodiment, the oligonucleotide compositions of the invention are contacted with human cells.

Oligonucleotide compositions of the invention can be contacted with cells in vitro, e.g., in a test tube or culture dish, (and may or may not be introduced into a subject) or in vivo, e.g., in a subject such as a mammalian subject. Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. *Nucleic Acids Research.* 21:3567). Enhanced delivery of oligonucleotides can also be mediated by the use of vectors (See e.g., Shi, Y. 2003. Trends Genet 2003 Jan. 19:9; Reichhart J M et al. Genesis. 2002. 34(1-2):1604, Yu et al. 2002. Proc. Natl. Acad Sci. USA 99:6047; Sui et al. 2002. Proc. Natl. Acad Sci. USA 99:5515) viruses, polyamine or polycation conjugates using compounds such as polylysine, protamine, or Ni, N12-bis (ethyl) spermine (see, e.g., Bartzatt, R. et al. 1989. *Biotechnol. Appl. Biochem.* 11:133; Wagner E. et al. 1992. *Proc. Natl. Acad. Sci.* 88:4255).

In certain embodiments, the miRNA of the invention may be delivered by using various beta-glucan containing particles, such as those described in US 2005/0281781 A1, WO 2006/007372, and WO 2007/050643 (all incorporated herein by reference). In certain embodiments, the beta-glucan particle is derived from yeast. In certain embodiments, the payload trapping molecule is a polymer, such as those with a molecular weight of at least about 1000 Da, 10,000 Da, 50,000 Da, 100 kDa, 500 kDa, etc. Preferred polymers include (without limitation) cationic polymers, chitosans, or PEI (polyethylenimine), etc.

Such beta-glucan based delivery system may be formulated for oral delivery, where the orally delivered beta-glucan/miRNA constructs may be engulfed by macrophages or other related phagocytic cells, which may in turn release the miRNA constructs in selected in vivo sites. Alternatively or in addition, the miRNA may changes the expression of certain macrophage target genes.

The optimal protocol for uptake of oligonucleotides will depend upon a number of factors, the most crucial being the type of cells that are being used. Other factors that are important in uptake include, but are not limited to, the nature and concentration of the oligonucleotide, the confluence of the cells, the type of culture the cells are in (e.g., a suspension culture or plated) and the type of media in which the cells are grown.

Encapsulating Agents

Encapsulating agents entrap oligonucleotides within vesicles. In another embodiment of the invention, an oligonucleotide may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotide's pharmacokinetic or toxicological properties.

For example, the oligonucleotides of the present invention may also be administered encapsulated in liposomes, pharmaceutical compositions wherein the active ingredient is contained either dispersed or variously present in corpuscles consisting of aqueous concentric layers adherent to lipidic layers. The oligonucleotides, depending upon solubility, may be present both in the aqueous layer and in the lipidic layer, or in what is generally termed a liposomic suspension. The hydrophobic layer, generally but not exclusively, comprises phopholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 nm to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a lipid delivery vehicle originally designed as a research tool, such as Lipofectin or LIPOFECTAMINE™ 2000, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

Complexing Agents

Complexing agents bind to the oligonucleotides of the invention by a strong but non-covalent attraction (e.g., an electrostatic, van der Waals, pi-stacking, etc. interaction). In one embodiment, oligonucleotides of the invention can be complexed with a complexing agent to increase cellular uptake of oligonucleotides. An example of a complexing agent includes cationic lipids. Cationic lipids can be used to deliver oligonucleotides to cells.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms. Alicyclic groups include cholesterol and other steroid groups. Cationic lipids can be prepared with a variety of counterions (anions) including, e.g., Cl$^-$, Br$^-$, I$^-$, F$^-$, acetate, trifluoroacetate, sulfate, nitrite, and nitrate.

Examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N—(N',N'-dimethylaminoethane)carbamoyl]cholesterol (DC-Chol), 2,3,-dioleyloxy-N-[2 (sperminecarboxamido)ethyl]-N,N-dimethyl-1-propan-aminium trifluoroacetate (DOSPA), 1,2-dimyristyloxypropyl-3-dimethyl-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosphorothioate oligonucleotide. (Vlassov et al., 1994, Biochimica et Biophysica Acta 1197:95-108). Oligonucleotides can also be complexed with, e.g., poly (L-lysine) or avidin and lipids may, or may not, be included in this mixture, e.g., steryl-poly (L-lysine).

Cationic lipids have been used in the art to deliver oligonucleotides to cells (see, e.g., U.S. Pat. Nos. 5,855,910; 5,851,548; 5,830,430; 5,780,053; 5,767,099; Lewis et al. 1996. Proc. Natl. Acad. Sci. USA 93:3176; Hope et al. 1998. Molecular Membrane Biology 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. Nos. 4,235,871; 4,501,728; 4,837,028; 4,737,323.

In one embodiment lipid compositions can further comprise agents, e.g., viral proteins to enhance lipid-mediated transfections of oligonucleotides (Kamata, et al., 1994. Nucl. Acids. Res. 22:536). In another embodiment, oligonucleotides are contacted with cells as part of a composition comprising an oligonucleotide, a peptide, and a lipid as taught, e.g., in U.S. Pat. No. 5,736,392. Improved lipids have also been described which are serum resistant (Lewis, et al., 1996. Proc. Natl. Acad. Sci. 93:3176). Cationic lipids and other complexing agents act to increase the number of oligonucleotides carried into the cell through endocytosis.

In another embodiment N-substituted glycine oligonucleotides (peptoids) can be used to optimize uptake of oligonucleotides. Peptoids have been used to create cationic lipid-like compounds for transfection (Murphy, et al., 1998. Proc. Natl. Acad. Sci. 95:1517). Peptoids can be synthesized using standard methods (e.g., Zuckermann, R. N., et al. 1992. J. Am. Chem. Soc. 114:10646; Zuckermann, R. N., et al. 1992. Int. J. Peptide Protein Res. 40:497). Combinations of cationic lipids and peptoids, liptoids, can also be used to optimize uptake of the subject oligonucleotides (Hunag, et al., 1998. Chemistry and Biology. 5:345). Liptoids can be synthesized by elaborating peptoid oligonucleotides and coupling the amino terminal submonomer to a lipid via its amino group (Hunag, et al., 1998. Chemistry and Biology. 5:345).

It is known in the art that positively charged amino acids can be used for creating highly active cationic lipids (Lewis et al. 1996. Proc. Natl. Acad. Sci. USA. 93:3176). In one embodiment, a composition for delivering oligonucleotides of the invention comprises a number of arginine, lysine, histidine or ornithine residues linked to a lipophilic moiety (see e.g., U.S. Pat. No. 5,777,153).

In another embodiment, a composition for delivering oligonucleotides of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used.

In one embodiment, a composition for delivering oligonucleotides of the invention comprises a natural or synthetic polypeptide having one or more gamma carboxyglutamic acid residues, or γ-Gla residues. These gamma carboxyglutamic acid residues may enable the polypeptide to bind to each other and to membrane surfaces. In other words, a polypeptide having a series of γ-Gla may be used as a general delivery modality that helps an RNAi construct to stick to whatever membrane to which it comes in contact. This may at least slow RNAi constructs from being cleared from the blood stream and enhance their chance of homing to the target.

The gamma carboxyglutamic acid residues may exist in natural proteins (for example, prothrombin has 10 γ-Gla residues). Alternatively, they can be introduced into the purified, recombinantly produced, or chemically synthesized polypeptides by carboxylation using, for example, a vitamin K-dependent carboxylase. The gamma carboxyglutamic acid residues may be consecutive or non-consecutive, and the total number and location of such gamma carboxyglutamic acid residues in the polypeptide can be regulated/fine tuned to achieve different levels of "stickiness" of the polypeptide.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment, the incubation of the cells with the mixture comprising a lipid and an oligonucleotide composition does not reduce the viability of the cells. Preferably, after the transfection period the cells are substantially viable. In one embodiment, after transfection, the cells are between at least about 70% and at least about 100% viable. In another embodiment, the cells are between at least about 80% and at least about 95% viable. In yet another embodiment, the cells are between at least about 85% and at least about 90% viable.

In one embodiment, oligonucleotides are modified by attaching a peptide sequence that transports the oligonucleotide into a cell, referred to herein as a "transporting peptide." In one embodiment, the composition includes an oligonucleotide which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. Cell 88:223).

Oligonucleotides can be attached to the transporting peptide using known techniques, e.g., (Prochiantz, A. 1996. *Curr. Opin. Neurobiol.* 6:629; Derossi et al. 1998. *Trends Cell Biol.* 8:84; Troy et al. 1996. *J. Neurosci.* 16:253), Vives et al. 1997. *J. Biol. Chem.* 272:16010). For example, in one embodiment, oligonucleotides bearing an activated thiol group are linked via that thiol group to a cysteine present in a transport peptide (e.g., to the cysteine present in the β turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. J Cell Biol. 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleomonomer and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_2$-$C_{20}$ alkenyl chains, $C_2$-$C_{20}$ alkynyl chains, peptides, and heteroatoms (e.g., S, O, NH, etc.). Other exemplary linkers include bifunctional crosslinking agents such as sulfosuccinimidyl-4-(maleimidophenyl)-butyrate (SMPB) (see, e.g., Smith et al. Biochem J 1991.276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics.* 18:559, and the references cited therein).

Targeting Agents

The delivery of oligonucleotides can also be improved by targeting the oligonucleotides to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

For instance, oligonucleotide conjugates to 6-phosphomannosylated proteins are internalized 20-fold more efficiently by cells expressing mannose 6-phosphate specific receptors than free oligonucleotides. The oligonucleotides may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. *Biochimica et Biophysica Acta* 1197:95-108).

In addition specific ligands can be conjugated to the polylysine component of polylysine-based delivery systems. For example, transferrin-polylysine, adenovirus-polylysine, and influenza virus hemagglutinin HA-2 N-terminal fusogenic peptides-polylysine conjugates greatly enhance receptor-mediated DNA delivery in eucaryotic cells. Mannosylated glycoprotein conjugated to poly(L-lysine) in aveolar macrophages has been employed to enhance the cellular uptake of oligonucleotides. Liang et al. 1999. *Pharmazie* 54:559-566.

Because malignant cells have an increased need for essential nutrients such as folic acid and transferrin, these nutrients can be used to target oligonucleotides to cancerous cells. For example, when folic acid is linked to poly(L-lysine) enhanced oligonucleotide uptake is seen in promyelocytic leukaemia (HL-60) cells and human melanoma (M-14) cells. Ginobbi et al. 1997. *Anticancer Res.* 17:29. In another example, liposomes coated with maleylated bovine serum albumin, folic acid, or ferric protoporphyrin IX, show enhanced cellular uptake of oligonucleotides in murine macrophages, KB cells, and 2.2.15 human hepatoma cells. Liang et al. 1999. *Pharmazie* 54:559-566.

Liposomes naturally accumulate in the liver, spleen, and reticuloendothelial system (so-called, passive targeting). By coupling liposomes to various ligands such as antibodies are protein A, they can be actively targeted to specific cell populations. For example, protein A-bearing liposomes may be pretreated with H-2K specific antibodies which are targeted to the mouse major histocompatibility complex-encoded H-2K protein expressed on L cells. (Vlassov et al. 1994. *Biochimica et Biophysica Acta* 1197:95-108).

Other in vitro and/or in vivo delivery of RNAi reagents are known in the art, and can be used to deliver the subject RNAi constructs. See, for example, U.S. patent application publications 20080152661, 20080112916, 20080107694, 20080038296, 20070231392, 20060240093, 20060178327, 20060008910, 20050265957, 20050064595, 20050042227, 20050037496, 20050026286, 20040162235, 20040072785, 20040063654, 20030157030, WO 2008/036825, WO04/065601, and AU2004206255B2, just to name a few (all incorporated by reference).

Administration

The optimal course of administration or delivery of the oligonucleotides may vary depending upon the desired result and/or on the subject to be treated. As used herein "administration" refers to contacting cells with oligonucleotides and can be performed in vitro or in vivo. The dosage of oligonucleotides may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the oligonucleotide in inducing the cleavage of a target RNA can be determined.

Any of the above-described oligonucleotide compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

Moreover, the present invention provides for administering the subject oligonucleotides with an osmotic pump providing continuous infusion of such oligonucleotides, for example, as described in Rataiczak et al. (1992 *Proc. Natl. Acad. Sci. USA* 89:11823-11827). Such osmotic pumps are commercially available, e.g., from Alzet Inc. (Palo Alto, Calif.). Topical administration and parenteral administration in a cationic lipid carrier are preferred.

With respect to in vivo applications, the formulations of the present invention can be administered to a patient in a variety of forms adapted to the chosen route of administration, e.g., parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended immediately prior to use. Lyophilized forms are also included in the invention.

Pharmaceutical preparations for topical administration include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration.

Pharmaceutical preparations for oral administration include powders or granules, suspensions or solutions in water or non-aqueous media, capsules, sachets or tablets. In addition, thickeners, flavoring agents, diluents, emulsifiers, dispersing aids, or binders may be used in pharmaceutical preparations for oral administration.

For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligonucleotides are formulated into conventional oral administration forms such as capsules, tablets, and tonics. For topical administration, the oligonucleotides of the invention are formulated into ointments, salves, gels, or creams as known in the art.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described oligonucleotides may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the oligonucleotide to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the oligonucleotide at the lymph node. The oligonucleotide can be modified to diffuse into the cell, or the liposome can directly participate in the delivery of either the unmodified or modified oligonucleotide into the cell.

The chosen method of delivery will result in entry into cells. Preferred delivery methods include liposomes (10-400 nm), hydrogels, controlled-release polymers, and other pharmaceutically applicable vehicles, and microinjection or electroporation (for ex vivo treatments).

The pharmaceutical preparations of the present invention may be prepared and formulated as emulsions. Emulsions are usually heterogeneous systems of one liquid dispersed in another in the form of droplets usually exceeding 0.1 µm in diameter. The emulsions of the present invention may contain excipients such as emulsifiers, stabilizers, dyes, fats, oils, waxes, fatty acids, fatty alcohols, fatty esters, humectants, hydrophilic colloids, preservatives, and anti-oxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montrnorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of oligonucleotides are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11:1385; Ho et al., J. Pharm. Sci., 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

In an embodiment, the present invention employs various penetration enhancers to affect the efficient delivery of nucleic acids, particularly oligonucleotides, to the skin of animals. Even non-lipophilic drugs may cross cell membranes if the membrane to be crossed is treated with a penetration enhancer. In addition to increasing the diffusion of non-lipophilic drugs across cell membranes, penetration enhancers also act to enhance the permeability of lipophilic drugs.

Five categories of penetration enhancers that may be used in the present invention include: surfactants, fatty acids, bile salts, chelating agents, and non-chelating non-surfactants. Other agents may be utilized to enhance the penetration of the administered oligonucleotides include: glycols such as ethylene glycol and propylene glycol, pyrrols such as 2-15 pyrrol, azones, and terpenes such as limonene, and menthone.

The oligonucleotides, especially in lipid formulations, can also be administered by coating a medical device, for example, a catheter, such as an angioplasty balloon catheter, with a cationic lipid formulation. Coating may be achieved, for example, by dipping the medical device into a lipid formulation or a mixture of a lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a patient, as appropriate. Alternatively, a lyophilized mixture of a lipid formulation may be specifically bound to the surface of the device. Such binding techniques are described, for example, in K. Ishihara et al., Journal of Biomedical Materials Research, Vol. 27, pp. 1309-1314 (1993), the disclosures of which are incorporated herein by reference in their entirety.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the oligonucleotides, the amount of lipid compound that is administered can vary and generally depends upon the amount of oligonucleotide agent being administered. For example, the weight ratio of lipid compound to oligonucleotide agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular oligonucleotide agent, and about 1 mg to about 100 mg of the lipid compositions, each per kilogram of patient body weight, is administered, although higher and lower amounts can be used.

The agents of the invention are administered to subjects or contacted with cells in a biologically compatible form suitable for pharmaceutical administration. By "biologically compatible form suitable for administration" is meant that the oligonucleotide is administered in a form in which any toxic effects are outweighed by the therapeutic effects of the oligonucleotide. In one embodiment, oligonucleotides can be administered to subjects. Examples of subjects include mammals, e.g., humans and other primates; cows, pigs, horses, and farming (agricultural) animals; dogs, cats, and other domesticated pets; mice, rats, and transgenic non-human animals.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

Dosage regime may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

Physical methods of introducing nucleic acids include injection of a solution containing the nucleic acid, bombardment by particles covered by the nucleic acid, soaking the cell or organism in a solution of the nucleic acid, or electroporation of cell membranes in the presence of the nucleic acid. A viral construct packaged into a viral particle would accomplish both efficient introduction of an expression construct into the cell and transcription of nucleic acid encoded by the expression construct. Other methods known in the art for introducing nucleic acids to cells may be used, such as lipid-mediated carrier transport, chemical-mediated transport, such as calcium phosphate, and the like. Thus the nucleic acid may be introduced along with components that perform one or more of the following activities: enhance nucleic acid uptake by the cell, inhibit annealing of single strands, stabilize the single strands, or otherwise increase inhibition of the target gene.

Nucleic acid may be directly introduced into the cell (i.e., intracellularly); or introduced extracellularly into a cavity, interstitial space, into the circulation of an organism, introduced orally or by inhalation, or may be introduced by bathing a cell or organism in a solution containing the nucleic acid. Vascular or extravascular circulation, the blood or lymph system, and the cerebrospinal fluid are sites where the nucleic acid may be introduced.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals.

Alternatively, vectors, e.g., transgenes encoding a siRNA of the invention can be engineered into a host cell or transgenic animal using art recognized techniques.

Another use for the nucleic acids of the present invention (or vectors or transgenes encoding same) is a functional analysis to be carried out in eukaryotic cells, or eukaryotic non-human organisms, preferably mammalian cells or organisms and most preferably human cells, e.g. cell lines such as HeLa or 293 or rodents, e.g. rats and mice. By administering a suitable nucleic acid of the invention which is sufficiently complementary to a target mRNA sequence to direct target-specific RNA interference, a specific knockout or knockdown phenotype can be obtained in a target cell, e.g. in cell culture or in a target organism.

Thus, a further subject matter of the invention is a eukaryotic cell or a eukaryotic non-human organism exhibiting a target gene-specific knockout or knockdown phenotype comprising a fully or at least partially deficient expression of at least one endogenous target gene wherein said cell or organism is transfected with at least one vector comprising DNA encoding an RNAi agent capable of inhibiting the expression of the target gene. It should be noted that the present invention allows a target-specific knockout or knockdown of several different endogenous genes due to the specificity of the RNAi agent.

Gene-specific knockout or knockdown phenotypes of cells or non-human organisms, particularly of human cells or non-human mammals may be used in analytic to procedures, e.g. in the functional and/or phenotypical analysis of complex physiological processes such as analysis of gene expression profiles and/or proteomes. Preferably the analysis is carried out by high throughput methods using oligonucleotide based chips.

Assays of Oligonucleotide Stability

In some embodiments, the oligonucleotides of the invention are stabilized, i.e., substantially resistant to endonuclease and exonuclease degradation. An oligonucleotide is defined as being substantially resistant to nucleases when it is at least about 3-fold more resistant to attack by an endogenous cellular nuclease, and is highly nuclease resistant when it is at least about 6-fold more resistant than a corresponding oligonucleotide. This can be demonstrated by showing that the oligonucleotides of the invention are substantially resistant to nucleases using techniques which are known in the art.

One way in which substantial stability can be demonstrated is by showing that the oligonucleotides of the invention function when delivered to a cell, e.g., that they reduce transcription or translation of target nucleic acid molecules, e.g., by measuring protein levels or by measuring cleavage of mRNA. Assays which measure the stability of target RNA can be performed at about 24 hours post-transfection (e.g., using Northern blot techniques, RNase Protection Assays, or QC-PCR assays as known in the art). Alternatively, levels of the target protein can be measured. Preferably, in addition to testing the RNA or protein levels of interest, the RNA or protein levels of a control, non-targeted gene will be measured (e.g., actin, or preferably a control with sequence similarity to the target) as a specificity control. RNA or protein measurements can be made using any art-recognized technique. Preferably, measurements will be made beginning at about 16-24 hours post transfection. (M. Y. Chiang, et al. 1991. J Biol Chem. 266:18162-71; T. Fisher, et al. 1993. Nucleic Acids Research. 21 3857).

The ability of an oligonucleotide composition of the invention to inhibit protein synthesis can be measured using techniques which are known in the art, for example, by detecting an inhibition in gene transcription or protein synthesis. For example, Nuclease S1 mapping can be performed. In another example, Northern blot analysis can be used to measure the presence of RNA encoding a particular protein. For example, total RNA can be prepared over a cesium chloride cushion (see, e.g., Ausebel et al., 1987. Current Protocols in Molecular Biology (Greene & Wiley, New York)). Northern blots can then be made using the RNA and probed (see, e.g., Id.). In another example, the level of the specific mRNA produced by the target protein can be measured, e.g., using PCR. In yet another example, Western blots can be used to measure the amount of target protein present. In still another embodiment, a phenotype influenced by the amount of the protein can be detected. Techniques for performing Western blots are well known in the art, see, e.g., Chen et al. J. Biol. Chem. 271:28259.

In another example, the promoter sequence of a target gene can be linked to a reporter gene and reporter gene transcription (e.g., as described in more detail below) can be monitored. Alternatively, oligonucleotide compositions that do not target a promoter can be identified by fusing a portion of the target nucleic acid molecule with a reporter gene so that the reporter gene is transcribed. By monitoring a change in the expression of the reporter gene in the presence of the oligonucleotide composition, it is possible to determine the effectiveness of the oligonucleotide composition in inhibiting the expression of the reporter gene. For example, in one embodiment, an effective oligonucleotide composition will reduce the expression of the reporter gene.

A "reporter gene" is a nucleic acid that expresses a detectable gene product, which may be RNA or protein. Detection of mRNA expression may be accomplished by Northern blotting and detection of protein may be accomplished by staining with antibodies specific to the protein. Preferred reporter genes produce a readily detectable product. A reporter gene may be operably linked with a regulatory DNA sequence such that detection of the reporter gene product provides a measure of the transcriptional activity of the regulatory sequence. In preferred embodiments, the gene product of the reporter gene is detected by an intrinsic activity associated with that product. For instance, the reporter gene may encode a gene product that, by enzymatic activity, gives rise to a detectable signal based on color, fluorescence, or luminescence. Examples of reporter genes include, but are not limited to, those coding for chloramphenicol acetyl transferase (CAT), luciferase, beta-galactosidase, and alkaline phosphatase.

One skilled in the art would readily recognize numerous reporter genes suitable for use in the present invention. These include, but are not limited to, chloramphenicol acetyltransferase (CAT), luciferase, human growth hormone (hGH), and beta-galactosidase. Examples of such reporter genes can be found in F. A. Ausubel et al., Eds., Current Protocols in Molecular Biology, John Wiley & Sons, New York, (1989). Any gene that encodes a detectable product, e.g., any product having detectable enzymatic activity or against which a specific antibody can be raised, can be used as a reporter gene in the present methods.

One reporter gene system is the firefly luciferase reporter system. (Gould, S. J., and Subramani, S. 1988. Anal. Biochem., 7:404-408 incorporated herein by reference). The luciferase assay is fast and sensitive. In this assay, a lysate of the test cell is prepared and combined with ATP and the substrate luciferin. The encoded enzyme luciferase catalyzes a rapid, ATP dependent oxidation of the substrate to generate a light-emitting product. The total light output is measured and is proportional to the amount of luciferase present over a wide range of enzyme concentrations.

CAT is another frequently used reporter gene system; a major advantage of this system is that it has been an extensively validated and is widely accepted as a measure of promoter activity. (Gorman C. M., Moffat, L. F., and Howard, B. H. 1982. Mol. Cell. Biol., 2:1044-1051). In this system, test cells are transfected with CAT expression vectors and incubated with the candidate substance within 2-3 days of the initial transfection. Thereafter, cell extracts are prepared. The extracts are incubated with acetyl CoA and radioactive chloramphenicol. Following the incubation, acetylated chloramphenicol is separated from nonacetylated form by thin layer chromatography. In this assay, the degree of acetylation reflects the CAT gene activity with the particular promoter.

Another suitable reporter gene system is based on immunologic detection of hGH. This system is also quick and easy to use. (Selden, R., Burke-Howie, K. Rowe, M. E., Goodman, H. M., and Moore, D. D. (1986), Mol. Cell, Biol., 6:3173-3179 incorporated herein by reference). The hGH system is advantageous in that the expressed hGH polypeptide is assayed in the media, rather than in a cell extract. Thus, this system does not require the destruction of the test cells. It will be appreciated that the principle of this reporter gene system is not limited to hGH but rather adapted for use with any polypeptide for which an antibody of acceptable specificity is available or can be prepared.

In one embodiment, nuclease stability of a double-stranded oligonucleotide of the invention is measured and compared to a control, e.g., an RNAi molecule typically used in the art (e.g., a duplex oligonucleotide of less than 25 nucleotides in length and comprising 2 nucleotide base overhangs) or an unmodified RNA duplex with blunt ends.
Therapeutic Use By inhibiting the expression of a gene, the oligonucleotide compositions of the present invention can be used to treat any disease involving the expression of a protein. Examples of diseases that can be treated by oligonucleotide compositions, just to illustrate, include: cancer, retinopathies, autoimmune diseases, inflammatory diseases (i.e., ICAM-1 related disorders, Psoriasis, Ulcerative Colitus, Crohn's disease), viral diseases (i.e., HIV, Hepatitis C), miRNA disorders, and cardiovascular diseases.

In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein. There are numerous medical conditions for which antisense therapy is reported to be suitable (see, e.g., U.S. Pat. No. 5,830,653) as well as respiratory syncytial virus infection (WO 95/22,553) influenza virus (WO 94/23,028), and malignancies (WO 94/08, 003). Other examples of clinical uses of antisense sequences are reviewed, e.g., in Glaser. 1996. Genetic Engineering News 16:1. Exemplary targets for cleavage by oligonucleotides include, e.g., protein kinase Ca, ICAM-1, c-raf kinase, p53, c-myb, and the bcr/abl fusion gene found in chronic myelogenous leukemia.

The subject nucleic acids can be used in RNAi-based therapy in any animal having RNAi pathway, such as human, non-human primate, non-human mammal, non-human vertebrates, rodents (mice, rats, hamsters, rabbits, etc.), domestic livestock animals, pets (cats, dogs, etc.), *Xenopus*, fish, insects (*Drosophila*, etc.), and worms (*C. elegans*), etc.

The invention provides methods for inhibiting or preventing in a subject, a disease or condition associated with an aberrant or unwanted target gene expression or activity, by administering to the subject a nucleic acid of the invention. If appropriate, subjects are first treated with a priming agent so as to be more responsive to the subsequent RNAi therapy. Subjects at risk for a disease which is caused or contributed to by aberrant or unwanted target gene expression or activity can be identified by, for example, any or a combination of diagnostic or prognostic assays known in the art. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject.

In another aspect, the invention pertains to methods of modulating target gene expression, protein expression or activity for therapeutic purposes. Accordingly, in an exemplary embodiment, the methods of the invention involve contacting a cell capable of expressing target gene with a nucleic acid of the invention that is specific for the target gene or protein (e.g., is specific for the mRNA encoded by said gene or specifying the amino acid sequence of said protein) such that expression or one or more of the activities of target protein is modulated. These methods can be performed in vitro (e.g., by culturing the cell with the agent), in vivo (e.g., by administering the agent to a subject), or ex vivo. The subjects may be first treated with a priming agent so as to be more responsive to the subsequent RNAi therapy if desired. As such, the present invention provides methods of treating a subject afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

Thus the therapeutic agents of the invention can be administered to subjects to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent. Pharmacogenomics deals with clinically significant hereditary variations in the response to drugs due to altered drug disposition and abnormal action in affected persons.

Examples of useful therapeutic molecules are described in U.S. Provisional Application No. 61/149,946, entitled "Minimum Length Triggers of RNA Interference," filed on Feb. 4, 2009, U.S. Provisional Application No. 61/224,031, entitled "Minimum Length Triggers of RNA Interference," filed on Jul. 8, 2009, and PCT Application No. PCT/US2009/005247, entitled "Reduced Size Self-Delivering RNAi Compounds," filed on Sep. 22, 2009, the disclosure of each of which is incorporated by reference herein for specific nucleotide sequences.

For the purposes of the invention, ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

According to the present invention, an isolated, or biologically pure, protein or nucleic acid molecule is a compound that has been removed from its natural milieu. As such, to "isolated" and "biologically pure" do not necessarily reflect the extent to which the compound has been purified. An isolated compound of the present invention can be obtained from its natural source, can be produced using molecular biology techniques or can be produced by chemical synthesis.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1: Transfection of PS Tail RNA Constructs

PS tail constructs were chemically synthesized as single stands (Trilink Biotechnologies, San Diego, Calif.) and annealed to form duplexes by mixing equal molar ratios of each strand, heating to 90° C. for 2 minutes and incubating at 37° C. for 1 hour. PS tail constructs were kept on ice after annealing and stored −20° C. The PS tail constructs were transfected into HEK293 cells (ATCC, Manassas, Va.) using the Lipofectamine RNAiMAX (Invitrogen, Carlsbad, Calif.) reagent according to manufacturer's instructions. In brief, RNA was diluted to a 12× concentration and then combined with a 12× concentration of Lipofectamine RNAiMAX to complex. The RNA and transfection reagent were allowed to complex at room temperature for 20 minutes and make a 6× concentration. While complexing, HEK293 cells were washed, trypsinized and counted. The cells were diluted to a concentration recommended by the manufacturer and previously described conditions which was at $1 \times 10^5$ cells/ml. When RNA has completed complexing with the RNAiMAX transfection reagent 20 ul of the complexes were added to the appropriate well of the 96-well plate in triplicate. Cells were added to each well (100 ul volume) to make the final cell count per well at $1 \times 10^4$ cells/well. The volume of cells diluted the 6× concentration of complex to 1× which was equal to a concentration noted (between 10-0.05 nM). Cells were incubated for 24 or 48 hours under normal growth conditions.

After 24 or 48 hour incubation cells were lysed and gene silencing activity was measured using the QuantiGene assay (Panomics, Freemont, Calif.) which employs bDNA hybridization technology. The assay was carried out according to manufacturer's instructions.

Annealing protocols are described in Elbashir, S. M., Harborth, J. et al. (2001), Nature 411(6836):494-8, the entire contents of which is incorporated herein by reference.

TABLE 1

Representative RNA molecules tested in Example 1

| Duplex ID | Sense strand sequence | Antisense strand sequence |
|---|---|---|
| A | mC.mU.mC.mU.mU.mC.mG.mG.mA.mA.mA.mG.A.C. U.mG.mU.mU.mC.mC.mA.mA.mA.mA.mA*dC*dC* dT*dT*dC*dC*dC*dT*dG*dA*dA*dG (SEQ ID NO: 1) | U.U.U.U.U.G.G.A.A.C.A.G.U.C. U.U.C.C.G.A.A.G.A.G (SEQ ID NO: 2) |
| B | mC.mU.mC.mU.mU.mC.mG.mG.mA.mA.mA.mG.m A.mC.U.G. U.mU.mC.mC.mA.mA*mA*mA*mA*dC*dC*dT*dT *dC*dC*dC*dT*dG*dA*dA*dG*dG*dT*dT*dC*dC *dT*dC*dC (SEQ ID NO: 3) | U.U.U.U.U.G.G.A.A.C.A.G.U.C. U.U.C.C.G.A.A.G.A.G (SEQ ID NO: 4) |
| C | mG.mC.mA.mC.mU.mC.mU.mG.mA.mU.mU.mG.A.C. A.mA.mA.mU.mA.mC.mG.mA.mU.mU.mU*dC*dC* dT*dT*dC*dC*dC*dT*dG*dA*dA*dG (SEQ ID NO: 5) | A.A.A.U.C.G.U.A.U.U.U.G.U.C. A.A.U.C.A.G.A.G.U.G.C (SEQ ID NO: 6) |
| D | mG.mC.mA.mC.mU.mC.mU.mG.mA.mU.mU.mG.A.C. A.mA.mA.mU.mA.mC.mG.mA.mU.mU.mU*dC*dC* dT*dT*dC*dC*dC*dT*dG*dA*dA*dG*dG*dT*dT* dC*dC*dT*dC*dC (SEQ ID NO: 7) | A.A.A.U.C.G.U.A.U.U.U.G.U.C. A.A.U.C.A.G.A.G.U.G.C (SEQ ID NO: 8) |
| E | P.mC.mU.mC.mU.mU.mC.mG.mG.mA.mA.mA.mG. A.C.U.mG.mU.mU.mC.mC.mA.mA.mA.mA.mA (SEQ ID NO: 9) | U.U.U.U.U.G.G.A.A.C.A.G.U.C. U.U.C.C.G.A.A.G.A.G (SEQ ID NO: 10) |
| F | dC*dC*dT*dT*dC*dC*dC*dT*dG*dA*dA*dG*mG. mC.mA.mC.mU.mC.mU.mG.mA.mU.mU.mG.A.C. A.mA.mA.mU.mA.mC.mG.mA.mU.mU.Mu (SEQ ID NO: 11) | A.A.A.U.C.G.U.A.U.U.U.G.U.C. A.A.U.C.A.G.A.G.U.G.C (SEQ ID NO: 12) |
| G | dC*dC*dT*dT*dC*dC*dC*dT*dG*dA*dA*dG*G. C.A.C.U.C.U.G.A.U.U.G.A.C.A.A.A.U.A. C.G.A.U.U.U (SEQ ID NO: 13) | A.A.A.U.C.G.U.A.U.U.U.G.U.C. A.A.U.C.A.G.A.G.U.G.C (SEQ ID NO: 14) |
| H | dC*dC*dT*dT*dC*dC*dC*dT*dG*dA*dA*dG*mC. mU.mC.mU.mU.mC.mG.mG.mA.mA.mA.mG.mA.C. U.G.mU.mU.mC.mC.mA.mA.mA.mA.mA. (SEQ ID NO: 15) | U.U.U.U.U.G.G.A.A.C.A.G.U.C. U.U.C.C.G.A.A.G.A.G (SEQ ID NO: 16) |
| I | dC*dC*dT*dT*dC*dC*dC*dT*dG*dA*dA*dG*C. U.C.U.U.C.G.A.A.A.G.A.C.U.G.U.U.C. | U.U.U.U.U.G.G.A.A.C.A.G.U.C. U.U.C.C.G.A.A.G.A.G |

TABLE 1-continued

Representative RNA molecules tested in Example 1

| Duplex ID | Sense strand sequence | Antisense strand sequence |
|---|---|---|
| | C.A.A.A.A.A (SEQ ID NO: 17) | (SEQ ID NO: 18) |

Key:
d deoxy ribose
P 5' phosphate
* phosphorothioate (PS) backbone linkage
. phosphodiester (PO) backbone linkage
m 2'O methyl modification
f 2' Fluoro modification
Chl Cholesterol Example 2: In Vivo Analysis of PS Tail RNA Constructs Intradermal Injection Studies Male C57BL/6 mice, age approximately 8 weeks, were administered a single dose of 300 ug (in 50 uL) of oligonucleotide via intradermal injection. 48 hours after injection, 3 mm biopsies at the injection site were taken for quantitation of target mRNA levels by qPCR. Administration of Duplex "N"-sd-rxRNA G2 (no cholesterol), containing more than 2 (i.e 6 phosphorothioates), demonstrated ~40% silencing compared to animals dosed with PBS. Comparison of this compound to Duplex "L"-sd-rxRNA GI (no phosphorothioates), shows that the phosphorothioate tail is necessary for cellular uptake and silencing activity in vivo (FIG. 11).

TABLE 2

Representative RNA molecules tested in Example 2

| Duplex ID | Sense strand sequence | Antisense strand sequence |
|---|---|---|
| J | mC.mU.G.mU.G.G.A.A.G.mU.mC.mU.A.Chl (SEQ ID NO: 19) | P.mU.A.G.A.fC.fU.fU.fC.fC. A.mC.A.G*A*A*mC*mU*mC* U (SEQ ID NO: 20) |
| K | mC.mU.G.mU.G.G.A.A.G.mU.mC.mU.A.Chl (SEQ ID NO: 21) | P.mU.A.G.A.C.U.U.C.C. A.mC.A.G*A*A*mC*mU*mC* U (SEQ ID NO: 22) |
| L | mC.mU.G.mU.G.G.A.A.G.mU.mC*mU*A.chl (SEQ ID NO: 23) | P.fU.A.G.A.fC.fU.fU.fC.fC.A.fC. A.G.A.A.fC.fU.fC.U (SEQ ID NO: 24) |
| M | mC.mU.G.mU.G.G.A.A.G.mU.mC.mU.A.Chl (SEQ ID NO: 25) | P.fU.A.G.A.fC.fU.fU.fC.fC.A.fC. A.G.A.A.fC.fU*fC*U (SEQ ID NO: 26) |
| N | mC.mU.G.mU.G.G.A.A.G.mU.mC.mU.A (SEQ ID NO: 27) | P.mU.A.G.A.fC.fU.fU.fC.fC. A.mC.A.G*A*A*mC*mU*mC* U (SEQ ID NO: 28) |
| O | Cy3.mC.mU.mC.mU.mU.mC.mG.mG.mA.mA.mA.mG. A.C.U.mG.mU.mU.mC.mC.mA.mA.mA.mA (SEQ ID NO: 29) | U.U.U.U.U.G.G.A.A.C.A.G. U.C.U.U.U.C.C.G.A.A.G.A. G (SEQ ID NO: 30) |
| P | mC.mU.G.mU.G.G.A.A.G.mU.mC*mU*A.chl (SEQ ID NO: 31) | P.fU.A.G.A.fC.fU.fU.fC.fC. A.fC*A*G*A*A*fC*fU*fC*U (SEQ ID NO: 32) |

Key:
d deoxy ribose
P 5' phosphate
* phosphorothioate backbone linkage
. phosphodiester backbone linkage
m 2'O methyl modification
f 2' Fluoro modification
Chl Cholesterol

Having thus described several aspects of at least one embodiment of this invention, it is to be appreciated various alterations, modifications, and improvements will readily occur to those skilled in the art. Such alterations, modifica- tions, and improvements are intended to be part of this disclosure, and are intended to be within the spirit and scope of the invention. Accordingly, the foregoing description and drawings are by way of example only.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety. This application incorporates by reference the entire contents, including all the drawings and all parts of the specification (including sequence listing or amino acid/polynucleotide sequences) of U.S. Provisional Application No. 61/135,855, filed on Jul. 24, 2008, entitled "SHORT HAIRPIN RNAI CONSTRUCTS AND USES THEREOF," U.S. Provisional Application No. 61/197,768, filed on Oct. 30, 2008, entitled "MINIRNA CONSTRUCTS AND USES THEREOF," U.S. Provisional Application No. 61/208,394, filed on Feb. 23, 2009, U.S. Provisional Application Ser. No. 61/209,429, filed Mar. 6, 2009, PCT Application No. PCT/US2009/ 004326, filed on Jul. 23, 2009, entitled "RNAi Constructs and Uses Thereof," U.S. Provisional Application No. 61/192,954, entitled "Chemically Modified Polyucleotides and Methods of Using the Same," filed on Sep. 22, 2008, U.S. Provisional Application No. 61/149,946, entitled "Minimum Length Triggers of RNA Interference," filed on Feb. 4, 2009, U.S. Provisional Application No. 61/224,031, entitled "Minimum Length Triggers of RNA Interference," filed on Jul. 8, 2009 and PCT Application No. PCT/US2009/ 005247, entitled "Reduced Size Self-Delivering RNAi Compounds," filed on Sep. 22, 2009.

What is claimed is:

1. An isolated double stranded nucleic acid molecule comprising a guide strand and a passenger strand, wherein the passenger strand is 8-16 continuous nucleotides in length, wherein the isolated double stranded nucleic acid molecule comprises a double stranded region that is 8-16 nucleotides in length, wherein the guide strand is 19-25 nucleotides in length, and wherein the double stranded region is connected through a cleavable chemical linker to a single stranded region of at least six phosphorothioate modified nucleotides.

2. The isolated double stranded nucleic acid molecule of claim 1, wherein the double stranded nucleic acid molecule includes at least one of the following properties:
   a) at least one 2' O methyl or 2' fluoro modification; and
   b) a lipophilic group.

3. An isolated double stranded nucleic acid molecule comprising a guide strand and a passenger strand, wherein the passenger strand is 8-16 continuous nucleotides in length, wherein the isolated double stranded nucleic acid molecule comprises a double stranded region that is 8-16 nucleotides in length, wherein the guide strand is 19-25 nucleotides in length, and wherein the double stranded region is connected through a cleavable chemical linker to a single stranded region of at least three phosphorothioate modified nucleotides.

4. The isolated double stranded nucleic acid molecule of claim 1 wherein the nucleic acid has one end having a single nucleotide single stranded region, optionally wherein the single stranded region is connected to the guide strand and/or wherein the nucleic acid has one blunt end.

5. The isolated double stranded nucleic acid molecule of claim 1 wherein the single stranded region occurs at the 3' end of the passenger strand, the 5' end of the passenger strand, the 3' end of the guide strand or the 5' end of the guide strand, and wherein the single stranded region is DNA or RNA.

6. The isolated double stranded nucleic acid molecule of claim 1 wherein the double stranded region of the nucleic acid molecule is a perfect duplex or the double stranded region of the nucleic acid molecule contains at least one bulge region.

7. The isolated double stranded nucleic acid molecule of claim 1 wherein the double stranded region contains at least one nucleotide that is phosphorothioate modified, the single stranded region comprises at least eight phosphorothioate modified nucleotides, and/or wherein the single stranded region comprises 9-17 phosphorothioate modified nucleotides.

8. The isolated double stranded nucleic acid molecule of claim 1 wherein the nucleic acid molecule is chemically modified, optionally wherein the chemical modification is 2' O methyl and/or 2' Fluoro and optionally wherein more than one chemical modification is present in the same molecule.

9. The isolated double stranded nucleic acid molecule of claim 8 wherein the chemical modification is on the passenger strand, and/or the guide strand.

10. The isolated double stranded nucleic acid molecule of claim 1 wherein the single stranded region has complementarity to a mammalian gene and/or wherein the single stranded region functions as an antisense molecule.

11. The isolated double stranded nucleic acid molecule of claim 1 wherein the single stranded region is at least twelve nucleotides long.

12. The isolated double stranded nucleic acid molecule of claim 1 wherein the nucleic acid is a bifunctional nucleic acid molecule, wherein the double stranded region functions in RNA interference and the single stranded region functions in antisense.

13. The isolated double stranded nucleic acid molecule of claim 1 wherein the guide strand has complementarity to a target gene, and wherein the guide strand has at least one 2' O-methyl modification or 2'-fluoro modification and/or wherein the passenger strand is 8-14 nucleotides long and has complementarity to the guide strand, wherein the passenger strand is linked to a lipophilic group.

14. A method for inhibiting the expression of a target gene in a mammalian cell, comprising contacting the mammalian cell with an isolated double stranded nucleic acid molecule of claim 1.

15. The method of claim 14 wherein the isolated double stranded nucleic acid molecule includes a chemical modification that increases stability, increases evasion of immune regulation and/or prevents off-target gene silencing.

16. A method of inducing RNAi in a subject comprising: administering to a subject an effective amount for inducing RNAi of an mRNA of a target gene, an isolated double stranded nucleic acid molecule of claim 1, optionally wherein the step of administering is systemic, intravenous, intraperitoneal, intradermal, topical, intranasal, inhalation, oral, intramucosal, local injection, subcutaneous, oral tracheal, or intraocular.

17. The method of claim 16, wherein the subject is a human and optionally wherein the target gene is PPIB, MAP4K4 or SOD1.

18. A composition of an isolated double stranded nucleic acid molecule of claim 1 for inhibiting the expression of a target gene or treating a disease associated with expression of the target gene.

19. The isolated double stranded nucleic acid molecule of claim 1, wherein the guide strand comprises a 5' phosphate modification.

20. The isolated double stranded nucleic acid molecule of claim 2, wherein the at least one 2' O methyl or 2' fluoro modification is located on a C and/or a U nucleotide in the double stranded region of the guide strand.

* * * * *

SEQUENCE LISTING

```
<160> NUMBER OF SEQ ID NOS: 32

<210> SEQ ID NO 1
<211> LENGTH: 37
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: 2'-O-methyl
<220> FEATURE:
<221> NAME/KEY: misc_feature
<222> LOCATION: (16)..(25)
<223> OTHER INFORMATION: 2'-O-methyl
<220> FEATURE:
<221> NAME/KEY: misc_feature
<222> LOCATION: (25)..(37)
<223> OTHER INFORMATION: phosphorothioate linkage
<220> FEATURE:
<221> NAME/KEY: misc_feature
<222> LOCATION: (1)..(25)
<223> OTHER INFORMATION: ribonucleotide
<220> FEATURE:
<221> NAME/KEY: misc_feature
<222> LOCATION: (26)..(37)
<223> OTHER INFORMATION: deoxyribonucleotide

<400> SEQUENCE: 1
cucuucggaa agacuguucc aaaaaccttc cctgaag                              37

<210> SEQ ID NO 2
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 2
uuuuuggaac agucuuuccg aagag                                          25

<210> SEQ ID NO 3
<211> LENGTH: 45
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(14)
```

```
<223> OTHER INFORMATION: 2'-O-methyl
<220> FEATURE:
<221> NAME/KEY: misc_feature
<222> LOCATION: (18)..(25)
<223> OTHER INFORMATION: 2'-O-methyl
<220> FEATURE:
<221> NAME/KEY: misc_feature
<222> LOCATION: (22)..(45)
<223> OTHER INFORMATION: phosphorothioate linkage
<220> FEATURE:
<221> NAME/KEY: misc_feature
<222> LOCATION: (1)..(25)
<223> OTHER INFORMATION: ribonucleotide
<220> FEATURE:
<221> NAME/KEY: misc_feature
<222> LOCATION: (26)..(45)
<223> OTHER INFORMATION: deoxyribonucleotide

<400> SEQUENCE: 3
cucuucggaa agacuguucc aaaaaccttc cctgaaggtt cctcc                    45

<210> SEQ ID NO 4
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 4
uuuuuggaac agucuuuccg aagag                                          25

<210> SEQ ID NO 5
<211> LENGTH: 37
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: 2'-O-methyl
<220> FEATURE:
<221> NAME/KEY: misc_feature
<222> LOCATION: (16)..(25)
<223> OTHER INFORMATION: 2'-O-methyl
<220> FEATURE:
<221> NAME/KEY: misc_feature
<222> LOCATION: (25)..(37)
<223> OTHER INFORMATION: phosphorothioate linkage
<220> FEATURE:
<221> NAME/KEY: misc_feature
<222> LOCATION: (1)..(25)
<223> OTHER INFORMATION: ribonucleotide
<220> FEATURE:
<221> NAME/KEY: misc_feature
<222> LOCATION: (26)..(37)
<223> OTHER INFORMATION: deoxyribonucleotide

<400> SEQUENCE: 5
gcacucugau ugacaaauac gauuuccttc cctgaag                             37

<210> SEQ ID NO 6
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 6
aaaucguauu ugucaaucag agugc                                          25
```

```
<210> SEQ ID NO 7
<211> LENGTH: 45
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: 2'-O-methyl
<220> FEATURE:
<221> NAME/KEY: misc_feature
<222> LOCATION: (16)..(25)
<223> OTHER INFORMATION: 2'-O-methyl
<220> FEATURE:
<221> NAME/KEY: misc_feature
<222> LOCATION: (25)..(45)
<223> OTHER INFORMATION: phosphorothioate linkage
<220> FEATURE:
<221> NAME/KEY: misc_feature
<222> LOCATION: (1)..(25)
<223> OTHER INFORMATION: ribonucleotide
<220> FEATURE:
<221> NAME/KEY: misc_feature
<222> LOCATION: (26)..(45)
<223> OTHER INFORMATION: deoxyribonucleotide

<400> SEQUENCE: 7
gcacucugau ugacaaauac gauuuccttc cctgaaggtt cctcc            45

<210> SEQ ID NO 8
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 8
aaaucguauu ugucaaucag agugc                                  25

<210> SEQ ID NO 9
<211> LENGTH: 25
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: 5'-phosphate

<400> SEQUENCE: 9
cucuucggaa agacuguucc aaaaa                                  25

<210> SEQ ID NO 10
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 10
uuuuuggaac agucuuuccg aagag                                  25

<210> SEQ ID NO 11
<211> LENGTH: 37
<212> TYPE: DNA
<213> ORGANISM: Artificial Sequence
<220> FEATURE:
<223> OTHER INFORMATION: synthetic oligonucleotide
<220> FEATURE:
```

```
<221> NAME/KEY: misc_feature
<222> LOCATION: (1)..(12)
<223> OTHER INFORMATION: deoxyribonucleotide
<220> FEATURE:
<221> NAME/KEY: misc_feature
<222> LOCATION: (1)..(13)
<223> OTHER INFORMATION: phosphorothioate linkage
<220> FEATURE:
<221> NAME/KEY: misc_feature
<222> LOCATION: (13)..(37)
<223> OTHER INFORMATION: ribonucleotide
<220> FEATURE:
<221> NAME/KEY: misc_feature
<222> LOCATION: (13)..(23)
<223> OTHER INFORMATION: 2'-O-methyl
<220> FEATURE:
<221> NAME/KEY: misc_feature
<222> LOCATION: (27)..(37)
<223> OTHER INFORMATION: 2'-O-methyl

<400> SEQUENCE: 11
ccttccctga aggcacucug auugacaaau acgauuu                              37

<210> SEQ ID NO 12
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 12
aaaucguauu ugucaaucag agugc                                           25

<210> SEQ ID NO 13
<211> LENGTH: 37
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: deoxyribonucleotide
<220> FEATURE:
<221> NAME/KEY: misc_feature
<222> LOCATION: (1)..(13)
<223> OTHER INFORMATION: phosphorothioate linkage
<220> FEATURE:
<221> NAME/KEY: misc_feature
<222> LOCATION: (13)..(37)
<223> OTHER INFORMATION: ribonucleotide

<400> SEQUENCE: 13
ccttccctga aggcacucug auugacaaau acgauuu                              37

<210> SEQ ID NO 14
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 14
aaaucguauu ugucaaucag agugc                                           25

<210> SEQ ID NO 15
<211> LENGTH: 37
<212> TYPE: DNA
<213> ORGANISM: Artificial Sequence
<220> FEATURE:
<223> OTHER INFORMATION: synthetic oligonucleotide
```

```
<220> FEATURE:
<221> NAME/KEY: misc_feature
<222> LOCATION: (1)..(12)
<223> OTHER INFORMATION: deoxyribonucleotide
<220> FEATURE:
<221> NAME/KEY: misc_feature
<222> LOCATION: (1)..(13)
<223> OTHER INFORMATION: phosphorothioate linkage
<220> FEATURE:
<221> NAME/KEY: misc_feature
<222> LOCATION: (13)..(37)
<223> OTHER INFORMATION: ribonucleotide
<220> FEATURE:
<221> NAME/KEY: misc_feature
<222> LOCATION: (13)..(25)
<223> OTHER INFORMATION: 2'-O-methyl
<220> FEATURE:
<221> NAME/KEY: misc_feature
<222> LOCATION: (29)..(37)
<223> OTHER INFORMATION: 2'-O-methyl

<400> SEQUENCE: 15
ccttccctga agcucuucgg aaagacuguu ccaaaaa                             37

<210> SEQ ID NO 16
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 16
uuuuuggaac agucuuuccg aagag                                          25

<210> SEQ ID NO 17
<211> LENGTH: 37
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(12)
<223> OTHER INFORMATION: deoxyribonucleotide
<220> FEATURE:
<221> NAME/KEY: misc_feature
<222> LOCATION: (1)..(13)
<223> OTHER INFORMATION: phosphorothioate linkage
<220> FEATURE:
<221> NAME/KEY: misc_feature
<222> LOCATION: (13)..(37)
<223> OTHER INFORMATION: ribonucleotide

<400> SEQUENCE: 17
ccttccctga agcucuucgg aaagacuguu ccaaaaa                             37

<210> SEQ ID NO 18
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 18
uuuuuggaac agucuuuccg aagag                                          25

<210> SEQ ID NO 19
<211> LENGTH: 13
<212> TYPE: RNA
<213> ORGANISM: Artificial Sequence
<220> FEATURE:
```

```
<223> OTHER INFORMATION: synthetic oligonucleotide
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (10)..(12)
<223> OTHER INFORMATION: 2'-O-methyl
<220> FEATURE:
<221> NAME/KEY: misc_feature
<222> LOCATION: (13)..(13)
<223> OTHER INFORMATION: 3'-cholesterol

<400> SEQUENCE: 19
cuguggaagu cua                                                         13

<210> SEQ ID NO 20
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: 5'-phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (5)..(9)
<223> OTHER INFORMATION: 2'-fluoro
<220> FEATURE:
<221> NAME/KEY: misc_feature
<222> LOCATION: (11)..(11)
<223> OTHER INFORMATION: 2'-o-methyl
<220> FEATURE:
<221> NAME/KEY: misc_feature
<222> LOCATION: (13)..(19)
<223> OTHER INFORMATION: phosphorothioate linkage
<220> FEATURE:
<221> NAME/KEY: misc_feature
<222> LOCATION: (16)..(18)
<223> OTHER INFORMATION: 2'-o-methyl

<400> SEQUENCE: 20
uagacuucca cagaacucu                                                   19

<210> SEQ ID NO 21
<211> LENGTH: 13
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (10)..(12)
<223> OTHER INFORMATION: 2'-O-methyl
<220> FEATURE:
<221> NAME/KEY: misc_feature
```

-continued

```
<222> LOCATION: (13)..(13)
<223> OTHER INFORMATION: 3'-cholesterol

<400> SEQUENCE: 21
cuguggaagu cua                                                          13

<210> SEQ ID NO 22
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: 5'-phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (13)..(19)
<223> OTHER INFORMATION: phosphorothioate linkage
<220> FEATURE:
<221> NAME/KEY: misc_feature
<222> LOCATION: (16)..(18)
<223> OTHER INFORMATION: 2'-O-methyl

<400> SEQUENCE: 22
uagacuucca cagaacucu                                                    19

<210> SEQ ID NO 23
<211> LENGTH: 13
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (10)..(12)
<223> OTHER INFORMATION: 2'-O-methyl
<220> FEATURE:
<221> NAME/KEY: misc_feature
<222> LOCATION: (11)..(13)
<223> OTHER INFORMATION: phosphorothioate linkage
<220> FEATURE:
<221> NAME/KEY: misc_feature
<222> LOCATION: (13)..(13)
<223> OTHER INFORMATION: 3'-cholesterol

<400> SEQUENCE: 23
cuguggaagu cua                                                          13

<210> SEQ ID NO 24
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
```

```
<221> NAME/KEY: misc_feature
<222> LOCATION: (1)..(1)
<223> OTHER INFORMATION: 5'-phosphate
<220> FEATURE:
<221> NAME/KEY: misc_feature
<222> LOCATION: (1)..(1)
<223> OTHER INFORMATION: 2'-fluoro
<220> FEATURE:
<221> NAME/KEY: misc_feature
<222> LOCATION: (5)..(9)
<223> OTHER INFORMATION: 2'-fluoro
<220> FEATURE:
<221> NAME/KEY: misc_feature
<222> LOCATION: (11)..(11)
<223> OTHER INFORMATION: 2'-fluoro
<220> FEATURE:
<221> NAME/KEY: misc_feature
<222> LOCATION: (16)..(18)
<223> OTHER INFORMATION: 2'-fluoro

<400> SEQUENCE: 24
uagacuucca cagaacucu                                               19

<210> SEQ ID NO 25
<211> LENGTH: 13
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (10)..(12)
<223> OTHER INFORMATION: 2'-O-methyl
<220> FEATURE:
<221> NAME/KEY: misc_feature
<222> LOCATION: (13)..(13)
<223> OTHER INFORMATION: 3'-cholesterol

<400> SEQUENCE: 25
cuguggaagu cua                                                     13

<210> SEQ ID NO 26
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: 5'-phosphate
<220> FEATURE:
<221> NAME/KEY: misc_feature
<222> LOCATION: (1)..(1)
<223> OTHER INFORMATION: 2'-fluoro
<220> FEATURE:
<221> NAME/KEY: misc_feature
<222> LOCATION: (5)..(9)
<223> OTHER INFORMATION: 2'-fluoro
<220> FEATURE:
<221> NAME/KEY: misc_feature
<222> LOCATION: (11)..(11)
<223> OTHER INFORMATION: 2'-fluoro
<220> FEATURE:
<221> NAME/KEY: misc_feature
<222> LOCATION: (16)..(18)
<223> OTHER INFORMATION: 2'-fluoro
```

```
<220> FEATURE:
<221> NAME/KEY: misc_feature
<222> LOCATION: (17)..(19)
<223> OTHER INFORMATION: phosphorothioate linkage

<400> SEQUENCE: 26
uagacuucca cagaacucu                                                    19

<210> SEQ ID NO 27
<211> LENGTH: 13
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (10)..(12)
<223> OTHER INFORMATION: 2'-O-methyl

<400> SEQUENCE: 27
cuguggaagu cua                                                          13

<210> SEQ ID NO 28
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: 5'-phosphate
<220> FEATURE:
<221> NAME/KEY: misc_feature
<222> LOCATION: (5)..(9)
<223> OTHER INFORMATION: 2'-fluoro
<220> FEATURE:
<221> NAME/KEY: misc_feature
<222> LOCATION: (11)..(11)
<223> OTHER INFORMATION: 2'-fluoro
<220> FEATURE:
<221> NAME/KEY: misc_feature
<222> LOCATION: (13)..(19)
<223> OTHER INFORMATION: phosphorothioate linkage
<220> FEATURE:
<221> NAME/KEY: misc_feature
<222> LOCATION: (16)..(18)
<223> OTHER INFORMATION: 2'-fluoro

<400> SEQUENCE: 28
uagacuucca cagaacucu                                                    19

<210> SEQ ID NO 29
<211> LENGTH: 25
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: 5'-Cy3
<220> FEATURE:
<221> NAME/KEY: misc_feature
<222> LOCATION: (1)..(12)
```

```
<223> OTHER INFORMATION: 2'-O-methyl
<220> FEATURE:
<221> NAME/KEY: misc_feature
<222> LOCATION: (16)..(25)
<223> OTHER INFORMATION: 2'-O-methyl

<400> SEQUENCE: 29
cucuucggaa agacuguucc aaaaa                                              25

<210> SEQ ID NO 30
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 30
uuuuuggaac agucuuuccg aagag                                              25

<210> SEQ ID NO 31
<211> LENGTH: 13
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (1)..(1)
<223> OTHER INFORMATION: 3'-cholesterol
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (10)..(12)
<223> OTHER INFORMATION: 2'-O-methyl
<220> FEATURE:
<221> NAME/KEY: misc_feature
<222> LOCATION: (11)..(13)
<223> OTHER INFORMATION: phosphorothioate linkage

<400> SEQUENCE: 31
cuguggaagu cua                                                           13

<210> SEQ ID NO 32
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: 5'-phosphate
<220> FEATURE:
<221> NAME/KEY: misc_feature
<222> LOCATION: (1)..(1)
<223> OTHER INFORMATION: 2'-fluoro
<220> FEATURE:
<221> NAME/KEY: misc_feature
<222> LOCATION: (5)..(9)
<223> OTHER INFORMATION: 2'-fluoro
<220> FEATURE:
<221> NAME/KEY: misc_feature
<222> LOCATION: (10)..(12)
<223> OTHER INFORMATION: 2'-O-methyl
<220> FEATURE:
<221> NAME/KEY: misc_feature
```

```
<222> LOCATION: (11)..(11)
<223> OTHER INFORMATION: 2'-fluoro
<220> FEATURE:
<221> NAME/KEY: misc_feature
<222> LOCATION: (11)..(19)
<223> OTHER INFORMATION: phosphorothioate linkage
<220> FEATURE:
<221> NAME/KEY: misc_feature
<222> LOCATION: (16)..(18)
<223> OTHER INFORMATION: 2'-fluoro

<400> SEQUENCE: 32
uagacuucca cagaacucu                                                  19
```